(12) United States Patent
Dhawan et al.

(10) Patent No.: US 8,785,170 B2
(45) Date of Patent: *Jul. 22, 2014

(54) VARIANT CBH2 CELLULASES AND RELATED POLYNUCLEOTIDES

(75) Inventors: Ish K. Dhawan, Foster City, CA (US); Erika N. Segraves, Sunnyvale, AZ (US)

(73) Assignee: Codexis, Inc., Redwood City, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 13/393,495

(22) PCT Filed: Aug. 31, 2010

(86) PCT No.: PCT/US2010/047324
§ 371 (c)(1),
(2), (4) Date: Feb. 29, 2012

(87) PCT Pub. No.: WO2011/028708
PCT Pub. Date: Mar. 10, 2011

(65) Prior Publication Data
US 2012/0156754 A1    Jun. 21, 2012

Related U.S. Application Data

(60) Provisional application No. 61/239,914, filed on Sep. 4, 2009.

(51) Int. Cl.
C12N 9/42 (2006.01)
C12N 15/80 (2006.01)
C12N 1/22 (2006.01)
C12N 9/22 (2006.01)

(52) U.S. Cl.
USPC ............. 435/209; 435/320.1; 435/252.3; 435/254.6; 435/254.2; 536/23.2

(58) Field of Classification Search
CPC ........ C12N 9/2437; C12N 9/42; C12N 15/80; C12N 1/22; C12N 9/242; C12N 9/2445; C12N 15/75; C12N 9/2434; Y02E 50/16; Y02E 50/10; Y02E 50/343; Y02E 50/17; C12Y 302/01091; C12Y 302/01004; C08L 97/02; C08L 5/14; C13K 1/02; D21C 5/005; C12P 7/10; C12P 2203/00
USPC ............. 435/209, 254.1, 254.3, 254.6, 252.3, 435/252.35, 254.2, 320.1; 536/23.2, 23.1
See application file for complete search history.

(56) References Cited

U.S. PATENT DOCUMENTS

| | | | |
|---|---|---|---|
| 4,486,553 A | 12/1984 | Wesch | |
| 4,683,202 A | 7/1987 | Mullis | |
| 5,426,039 A | 6/1995 | Wallace et al. | |
| 5,648,263 A | 7/1997 | Schulein et al. | |
| 5,776,757 A | 7/1998 | Schulein et al. | |
| 6,117,679 A | 9/2000 | Stemmer | |
| 6,376,246 B1 | 4/2002 | Crameri et al. | |
| 6,586,182 B1 | 7/2003 | Patten et al. | |
| 7,244,605 B2 | 7/2007 | Harris et al. | |
| 7,783,428 B2 | 8/2010 | Gustafsson et al. | |
| 7,785,854 B2 | 8/2010 | St-Pierre et al. | |
| 8,008,056 B2 | 8/2011 | Aehle et al. | |
| 2002/0164730 A1 | 11/2002 | Perdices et al. | |
| 2008/0213835 A1 | 9/2008 | Wu et al. | |
| 2008/0220990 A1 | 9/2008 | Fox | |
| 2009/0312196 A1 | 12/2009 | Colbeck et al. | |
| 2010/0267088 A1 | 10/2010 | Pollack et al. | |

FOREIGN PATENT DOCUMENTS

| | | |
|---|---|---|
| EP | 0137280 B1 | 3/1992 |
| WO | 95/22625 A1 | 8/1995 |
| WO | 97/00078 A1 | 1/1997 |
| WO | 97/35966 A1 | 10/1997 |
| WO | 98/27230 A1 | 6/1998 |
| WO | 01/75767 A2 | 10/2001 |
| WO | 03/075129 A2 | 9/2003 |
| WO | 2004/048592 A2 | 6/2004 |
| WO | 2006/074005 A2 | 7/2006 |
| WO | 2008/042876 A2 | 4/2008 |
| WO | 2008/095033 A2 | 8/2008 |

OTHER PUBLICATIONS

Park et al Cloning and Sequencing of an Exoglucanase Gene from *Streptomyces* sp. M23, and Its Expression in *Streptomyces lividans* TK-24. Journal of Bioscience and Bioengineering 2005, vol. 99, No. 4, 434-436. 2005.*
UniProt B5HPK9 dated Oct. 14, 2008.
Adams, S.P., et al., "Hindered dialkylamino nucleoside phosphite reagents in the synthesis of two DNA 51-mers," J. Am. Chem. Soc., 105:661 (1983).
Altschul, S.F., et al., "Gapped BLAST and PSI-BLAST: a new generation of protein database search programs," Nucleic Acids Res., 25(17):3389-3402 (1997).
Arnheim, N., et al., "Polymerase Chain Reaction," C&EN, pp. 36-47 (1990).
Barringer, K.J., et al., "Blunt-end and single-strand ligations by *Escherichia coli* ligase: influence on an in vitro amplification scheme," Gene, 89:117-122 (1990).
Beaucage, S.L., et al., "Deoxynucleoside phosphoamidites—A new class of key intermediates for deoxypolynucleotide synthesis," Tetrahedron Letters, 22(20):1859-62 (1981).
Boel, E., et al., "Two different types of intervening sequences in the glucoamylase gene from *Aspergillus niger*," EMBO J., 3(7):1581-1585 (1984).
Botstein, D., et al., "Strategies and applications of in vitro mutagenesis," Science, 229(4719):1193-1201 (1985).

(Continued)

*Primary Examiner* — Kagnew H Gebreyesus
(74) *Attorney, Agent, or Firm* — Codexis, Inc.

(57) ABSTRACT

The invention provides variants of a *Streptomyces* sp. CBH2 that have improved properties compared to the wild type enzyme and methods of using the variants in the hydrolysis of substrates comprising cellulose.

23 Claims, 3 Drawing Sheets

(56) References Cited

OTHER PUBLICATIONS

Brigham, J.S., et al., "Hemicellulases: Diversity and Applications," in Handbook on Bioethanol (C. Wyman ed.) pp. 119-141, Taylor and Francis, Washington DC, (1995).
Carter, P., "Site-directed mutagenesis," Biochem. J., 237:1-7 (1986).
Caruthers, M.H., et al., "Chemical Synthesis and Biological Studies on Mutated Gene-control Regions," Cold Spring Harbor Symp. Quant. Biol., 47:411-418 (1982).
Case, M.E. et al., "Efficient transformation of *Neurospora crassa* by utilizing hybrid plasmid DNA," Proc. Natl. Acad. Sci. USA, 76(10):5259-5263 (1979).
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling,"Nat. Biotechnol., 14(3):315-319 (1996).
Crameri, A., et al., "Molecular evolution of an arsenate detoxification pathway by DNA shuffling," Nat. Biotechnol., 15 (5):436-438 (1997).
Dale, S.J. et al., "Oligonucleotide-directed random mutagenesis using the phosphorothioate method," Methods Mol. Biol., 57:369-74 (1996).
Dayhoff, M.O., et al. , "A model of evolutionary change in proteins" in "Atlas of Protein Sequence and Structure," vol. 5, Suppl. 3 , pp. 345-352, Natl. Biomed. Res. Round., Washington, D.C. (1978).
Duff, S.J.B., et al., "Bioconversion of Forest Products Industry Waste Cellulosics to Fuel Ethanol: A Review," Biores. Technol., 55: 1-33 (1996).
Foreman, P.K., et al., "Transcriptional Regulation of Biomass-degrading Enzymes in the Filamentous Fungus *Trichoderma reesei*," J. Biol. Chem., 278(34):31988-31997 (2003).
Fox, R. , "Directed molecular evolution by machine learning and the influence of nonlinear interactions," J. Theor. Biol., 234(2):187-199 (2005).
Fox, R., et al., "Optimizing the search algorithm for protein engineering by directed evolution," Protein Eng., 16 (8):589-597 (2003).
Gollapalli, L.E., et al., "Predicting digestibility of ammonia fiber explosion (AFEX)-treated rice straw," Appl. Biochem. Biotechnol., 98-100:23-35 (2002).
Guatelli, J.C., et al., "Isothermal, in vitro amplification of nucleic acids by a multienzyme reaction modeled after retroviral replication," Proc. Natl. Acad. Sci. USA, 87:1874-1878 (1990).
Heanut, A., et al., "Analysis and predictions from *Escherichia coli* sequences, or *E. coli* in silico," in *Escherichia coli* and *Salmonella*, ASM Pres, Washington D.C., pp. 2047-2066 (1987).
Henikoff, S., et al. "Amino acid substitution matrices from protein blocks," Proc. Natl. Acad. Sci. USA, 89:10915-10919 (1992).
Johnstone, I.L., et al., "Cloning an *Aspergillus nidulans* developmental gene by transformation," EMBO J., 4 (5):1307-1311 (1985).
Kelly, J.M., et al., "Transformation of *Asoergillus niger* by the amdS gene of *Aspergillus nidulans*," EMBO J., 4 (2):475-479 (1985).
Kinsey, J.A., et al., "Transformation of *Neurospora crassa* with the Cloned am (Glutamate Dehydrogenase) Gene", Molecular and Cellular Biology, 4:117-122 (1984).
Kramer, B., et al., "Different base/base mismatches are corrected with different efficiencies by the methyl-directed DNA mismatch-repair system of *E. coli*," Cell, 38(3):879-887 (1984).
Kumar, A., et al., "Optimizing the use of cellulase enzymes in finishing cellulosic fabrics," Textile Chemist and Colorist, 29:37-4 (1997).
Kwoh, D.Y. et al., "Transcription-based amplification system and detection of amplified human immunodeficiency virus type 1 with a bead-based sandwich hybridization format," Proc. Natl. Acad. Sci. USA, 86:1173-1177 (1989).
Ladisch, M.R., et al., "Process considerations in the enzymatic hydrolysis of biomass," Enzyme Microb. Technol., 5:82 (1983).
Landegren, U., et al., "A Ligase-Mediated Gene Detection Technique," Science, 241:1077-1080 (1988).
Ling, M.M., et al., "Approaches to DNA mutagenesis: an overview," Anal. Biochem., 254(2):157-78 (1997).
Lomeli, H., et al., "Quantitative Assays Based on the Use of Replicatable Hybridization Probes," J. Clin. Chem, 35 (9): 1826-1831 (1989).
Mase, T., et al., "Purification, characterization, and a potential application of beta-gludosidase from *Asperfillus pulverulentus* YM-80," J. Appl. Glycosci., 51:211-216 (2004).
Matthes, H.W.D., et al., "Simultaneous rapid chemical synthesis of over one hundred oligonucleotides on a microscale," EMBO J., 3(4):801-05 (1984).
Minshull, J., et al., "Protein evolution by molecular breeding," Current Opinion in Chemical Biology, 3:284-290 (1999).
Nunberg, J.H., et al., "Molecular Cloning and Characterization of the Glucoamylase Gene of *Aspergillus awamori*," Mol. Cell Biol., 4(11):2306-2315 (1984).
Park, C-S., et al., "Cloning and Sequencing of an Exoglucanase Gene from *Streptomyces* sp. M23, and Its Expression in *Streptomyces lividans* TK-24," J. Bioscience and Bioengineering, 99:434-436 (2005).
Ricciardelli, C., et al., "Development and characterization of primary cultures of smooth muscle cells from the fibromuscular stroma of the guinea pig prostate," In vitro Cell Dev. Biol., 25:1016-1024 (1989).
Robert, "Amplification of the nucleic acid sequence: The choices multiply," The Journal of NIH Research, 3:81-94 (1991).
Rygus, T., et al., "Inducible high-level expression of heterologous genes in *Bacillus megaterium* using the regulatory elements of the xylose-utilization operon," Appl. Microbiol. Biotechnol., 35(5):594-599 (1991).
Sassner, P., et al., "Bioethanol production based on simultaneous saccharification and fermentation of steam pretreated Salix at high dry-matter content," Enzyme Microb. Technol., 39:756-762 (2006).
Sheir-Neiss, G., et al., "Characterization of the secreted cellulases of *Trichoderma reesei* wild type and mutants during controlled fermentations," Appl. Microbiol. Biotechnol., 20:46-53 (1984).
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Sooknanan, R., et al., "NASBRA: A detection and amplification system uniquely suited for RNA," Biotechnology, 13:563-564 (1995).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Teymouri, F., et al., "Optimization of the ammonia fiber explosion (AFEX) treatment parameters for enzymatic hydrolysis of corn stover," Biores. Technol., 96:2014-2018 (2005).
Tilburn, J., et al., "Transformation by integration in *Asperfillus nidulans*," Gene, 26:205-221 (1982).
Van Brunt, J., "Amplifying Genes: PCR and its alternatives," Biotechnology, 8:291-294 (1990).
Wells, J.A., et al., "Cassette mutagenesis: an efficient method for generation of multiple mutations at defined sites," Gene, 34:315-323 (1985).
Wu, D.Y., et al., "The Ligation Amplification Reaction (LAR)—Amplification of Specific DNA Sequences Using Sequential Rounds of Template-Dependent Ligation," Genomics, 4:560 (1989).
Yanai, T., et al., "Isolation and Properties of Beta-Glucosidase Produced by *Debaryomyces hansenii* and Its Application in Winemaking," Am. J. Enol. Eitic., 50(3):231-235 (1999).
Yelton, M.M., et al., "Transformation of *Aspergillus nidulans* by using a trpC plasmid," Proc. Natl. Acad. Sci. USA, 81:1470-1474 (1984).
Zhang, J-H., et al., "Directed evolution of a fucosidase from a galactosidase by DNA shuffling and screening ,"Proc. Nat. Acad. Sci., U.S.A., 94:4504-4509 (1997).
UniProt entry: Q9KH72_THEFU (Submitted by Ai et al.; May 2000); Retrieved on Feb. 8, 2011 from URL: <http://www.uniprot.org/uniprot/Q9KH72>.
UniProt entry: Q8VLR1_9ACTO (Submitted by Park et al.; Jan. 2002); Retrieved on Nov. 1, 2010 from URL: <http://www.uniprot.org/uniprot/Q8VLR1>.

\* cited by examiner

Figure 1A

**ATGAAAAAGAAAAAACAGGCTTTAAAGGTATTATTATCAGTTGGTATCCTTTCTTC
ATCATTTGCTTTTGCACATACGAGCAGTGCC**<u>*GCGACTAGT*</u>ATGGGGCCTGCTGCAC
CTACTGCACGTGTGGATAATCCTTATGTAGGCGCGACAATGTACGTAAATCCAGAA
TGGTCAGCTCTTGCTGCTTCGGAACCAGGTGGTGATCGTGTTGCAGATCAACCTAC
GGCTGTTTGGTTAGATCGTATTGCAACTATTGAAGGTGTTGATGGAAAAATGGGAT
TACGAGAACATCTTGATGAAGCGTTACAACAAAAAGGAAGCGGAGAACTTGTGGTA
CAGTTAGTAATTTATGATTTACCTGGTCGTGATTGCGCGGCTCTTGCTAGTAATGG
TGAATTAGGTCCTGATGAATTAGATCGATATAAAGCGAATATATTGATCCGATTG
CAGACATTTTATCGGATTCCAAATATGAAGGACTTCGTATTGTTACGGTTATTGAA
CCAGACAGCTTACCTAATTTAGTAACAAACGCAGGTGGTACAGATACAACGACAGA
AGCATGTACTACTATGAAAGCAAACGGTAATTATGAAAAGGGGTATCGTATGCGC
TTTCTAAATTAGGTGCAATTCCGAACGTATACAACTATATTGATGCTGCTCATCAT
GGATGGTTAGGATGGGACACAAATTTAGGGCCATCCGTACAGGAATTTTATAAAGT
GGCAACATCAAATGGCGCATCCGTTGATGATGTGGCGGGATTTGCAGTCAATACAG
CTAATTATTCACCTACTGTAGAACCTTATTTTACGGTTTCAGATACGGTGAATGGG
CAGACGGTACGTCAATCTAAATGGGTTGACTGGAATCAATACGTAGATGAACAAAG
TTATGCGCAGGCTTTACGAAACGAAGCTGTCGCCGCTGGATTTAATAGCGATATTG
GTGTGATTATTGATACATCCCGAAATGGATGGGGTGGTTCAGATCGCCCTTCAGGG
CCTGGCCCTCAAACTTCCGTAGATGCTTATGTAGATGGATCACGAATTGATCGTCG
CGTTCATGTAGGAAATTGGTGTAATCAGTCTGGAGCAGGCTTAGGTGAAAGACCAA
CAGCAGCACCAGCTAGCGGGATTGATGCATATACATGGATTAAACCGCCGGGCGAA
TCTGATGGAAATTCAGCTCCGGTTGATAATGACGAAGGAAAAGGATTTGACCAAAT
GTGTGATCCTAGCTACCAGGGAAACGCTCGCAATGGCTACAATCCTTCAGGAGCGT
TACCTGATGCACCATTAAGTGGACAATGGTTTTCGGCACAATTTCGTGAATTAATG
CAAAATGCATATCCTCCATTATCTTGA        (SEQ ID NO: 1)

<u>MKKKKQALKVLLSVGILSSSFAFAHTSSAA</u>TSMGPAAPTARVDNPYVGATMYVNPE
WSALAASEPGGDRVADQPTAVWLDRIATIEGVDGKMGLREHLDEALQQKGSGELVV
QLVIYDLPGRDCAALASNGELGPDELDRYKSEYIDPIADILSDSKYEGLRIVTVIE
PDSLPNLVTNAGGTDTTTEACTTMKANGNYEKGVSYALSKLGAIPNVYNYIDAAHH
GWLGWDTNLGPSVQEFYKVATSNGASVDDVAGFAVNTANYSPTVEPYFTVSDTVNG
QTVRQSKWVDWNQYVDEQSYAQALRNEAVAAGFNSDIGVIIDTSRNGWGGSDRPSG
PGPQTSVDAYVDGSRIDRRVHVGNWCNQSGAGLGERPTAAPASGIDAYTWIKPPGE
SDGNSAPVDNDEGKGFDQMCDPSYQGNARNGYNPSGALPDAPLSGQWFSAQFRELM
QNAYPPLS
(SEQ ID NO: 2)

Figure 2A

ATGGGGCCTGCTGCACCTACTGCACGTGTGGATAATCCTTATGTAGGCGCGACAAT
GTACGTAAATCCAGAATGGTCAGCTCTTGCTGCTTCGGAACCAGGTGGTGATCGTG
TTGCAGATCAACCTACGGCTGTTTGGTTAGATCGTATTGCAACTATTGAAGGTGTT
GATGGAAAAATGGGATTACGAGAACATCTTGATGAAGCGTTACAACAAAAAGGAAG
CGGAGAACTTGTGGTACAGTTAGTAATTTATGATTTACCTGGTCGTGATTGCGCGG
CTCTTGCTAGTAATGGTGAATTAGGTCCTGATGAATTAGATCGATATAAAAGCGAA
TATATTGATCCGATTGCAGACATTTTATCGGATTCCAAATATGAAGGACTTCGTAT
TGTTACGGTTATTGAACCAGACAGCTTACCTAATTTAGTAACAAACGCAGGTGGTA
CAGATACAACGACAGAAGCATGTACTACTATGAAAGCAAACGGTAATTATGAAAAA
GGGGTATCGTATGCGCTTTCTAAATTAGGTGCAATTCCGAACGTATACAACTATAT
TGATGCTGCTCATCATGGATGGTTAGGATGGGACACAAATTTAGGGCCATCCGTAC
AGGAATTTTATAAAGTGGCAACATCAAATGGCGCATCCGTTGATGATGTGGCGGGA
TTTGCAGTCAATACAGCTAATTATTCACCTACTGTAGAACCTTATTTTACGGTTTC
AGATACGGTGAATGGGCAGACGGTACGTCAATCTAAATGGGTTGACTGGAATCAAT
ACGTAGATGAACAAAGTTATGCGCAGGCTTTACGAAACGAAGCTGTCGCCGCTGGA
TTTAATAGCGATATTGGTGTGATTATTGATACATCCCGAAATGGATGGGGTGGTTC
AGATCGCCCTTCAGGGCCTGGCCCTCAAACTTCCGTAGATGCTTATGTAGATGGAT
CACGAATTGATCGTCGCGTTCATGTAGGAAATTGGTGTAATCAGTCTGGAGCAGGC
TTAGGTGAAAGACCAACAGCAGCACCAGCTAGCGGGATTGATGCATATACATGGAT
TAAACCGCCGGGCGAATCTGATGGAAATTCAGCTCCGGTTGATAATGACGAAGGAA
AAGGATTTGACCAAATGTGTGATCCTAGCTACCAGGGAAACGCTCGCAATGGCTAC
AATCCTTCAGGAGCGTTACCTGATGCACCATTAAGTGGACAATGGTTTTCGGCACA
ATTTCGTGAATTAATGCAAATGCATATCCTCCATTATCTTGA
(SEQ ID NO: 3)

Figure 2B

MGPAAPTARVDNPYVGATMYVNPEWSALAASEPGGDRVADQPTAVWLDRIATIEG
VDGKMGLREHLDEALQQKGSGELVVQLVIYDLPGRDCAALASNGELGPDELDRYK
SEYIDPIADILSDSKYEGLRIVTVIEPDSLPNLVTNAGGTDTTTEACTTMKANGN
YEKGVSYALSKLGAIPNVYNYIDAAHHGWLGWDTNLGPSVQEFYKVATSNGASVD
DVAGFAVNTANYSPTVEPYFTVSDTVNGQTVRQSKWVDWNQYVDEQSYAQALRNE
AVAAGFNSDIGVIIDTSRNGWGGSDRPSGPGPQTSVDAYVDGSRIDRRVHVGNWC
NQSGAGLGERPTAAPASGIDAYTWIKPPGESDGNSAPVDNDEGKGFDQMCDPSYQ
GNARNGYNPSGALPDAPLSGQWFSAQFRELMQNAYPPLS
(SEQ ID NO: 4)

Figures 3A and B
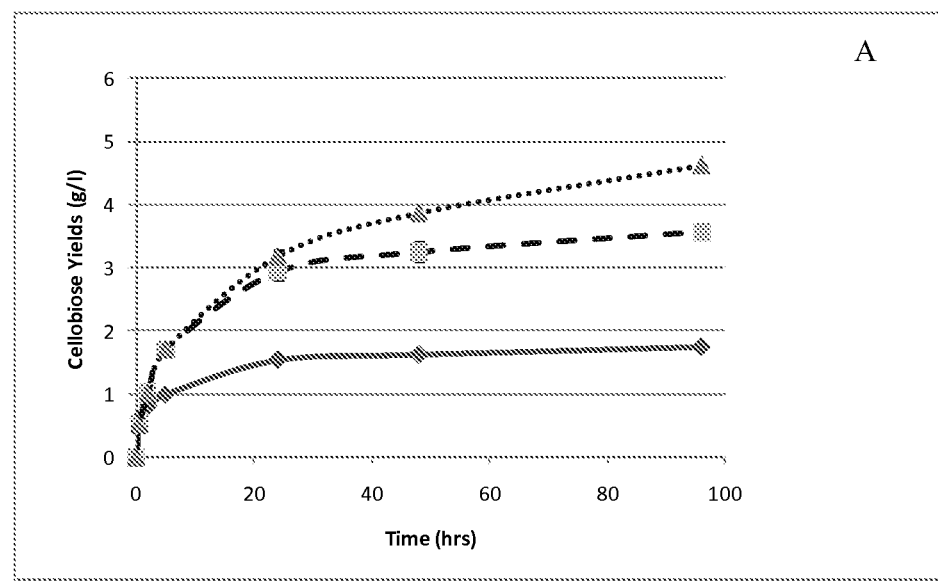
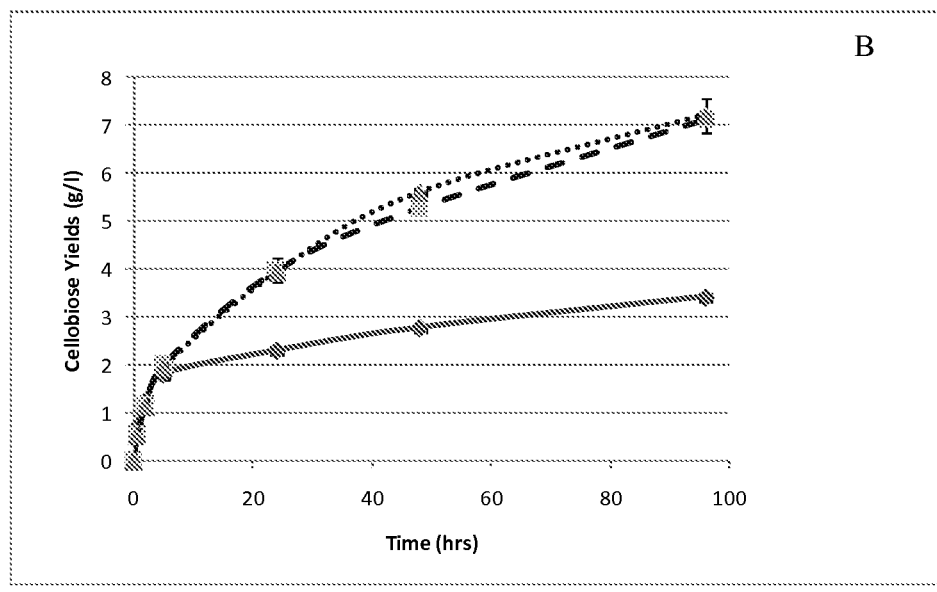

SEQUENCE LISTING

```
<160> NUMBER OF SEQ ID NOS: 8

<210> SEQ ID NO 1
<211> LENGTH: 1371
<212> TYPE: DNA
<213> ORGANISM: Artificial
<220> FEATURE:
<223> OTHER INFORMATION: Synthetic DNA codon optimized polynucleotide
      sequence encoding a Streptomyces sp M23 CBH2 and having the NprM
      signal peptide and restriction site

<400> SEQUENCE: 1
atgaaaaaga aaaacaggc tttaaaggta ttattatcag ttggtatcct ttcttcatca     60
tttgcttttg cacatacgag cagtgccgcg actagtatgg ggcctgctgc acctactgca    120
cgtgtggata tccttatgt aggcgcgaca atgtacgtaa atccagaatg gtcagctctt    180
gctgcttcgg aaccaggtgg tgatcgtgtt gcagatcaac ctacggctgt ttggttagat    240
cgtattgcaa ctattgaagg tgttgatgga aaaatgggat tacgagaaca tcttgatgaa    300
gcgttacaac aaaaaggaag cggagaactt gtggtacagt tagtaattta tgatttacct    360
```

-continued

```
ggtcgtgatt gcgcggctct tgctagtaat ggtgaattag gtcctgatga attagatcga    420
tataaaagcg aatatattga tccgattgca gacattttat cggattccaa atatgaagga    480
cttcgtattg ttacggttat tgaaccagac agcttaccta atttagtaac aaacgcaggt    540
ggtacagata caacgacaga agcatgtact actatgaaag caaacggtaa ttatgaaaaa    600
ggggtatcgt atgcgctttc taaattaggt gcaattccga acgtatacaa ctatattgat    660
gctgctcatc atggatggtt aggatgggac acaaatttag gccatccgt acaggaattt    720 tataaagtgg caacatcaaa tggcgcatcc gttgatgatg tggcgggatt tgcagtcaat    780
acagctaatt attcacctac tgtagaacct tattttacgg tttcagatac ggtgaatggg    840
cagacggtac gtcaatctaa atgggttgac tggaatcaat acgtagatga acaaagttat    900
gcgcaggctt tacgaaacga agctgtcgcc gctggattta atagcgatat tggtgtgatt    960
attgatacat cccgaaatgg atggggtggt tcagatcgcc cttcagggcc tggccctcaa   1020
acttccgtag atgcttatgt agatggatca cgaattgatc gtcgcgttca tgtaggaaat   1080
tggtgtaatc agtctggagc aggcttaggt gaaagaccaa cagcagcacc agctagcggg   1140
attgatgcat atacatggat taaaccgccg ggcgaatctg atggaaattc agctccggtt   1200
gataatgacg aaggaaaagg atttgaccaa atgtgtgatc ctagctacca gggaaacgct   1260
cgcaatggct acaatccttc aggagcgtta cctgatgcac cattaagtgg acaatggttt   1320
tcggcacaat ttcgtgaatt aatgcaaaat gcatatcctc cattatcttg a            1371
```

<210> SEQ ID NO 2
<211> LENGTH: 456
<212> TYPE: PRT
<213> ORGANISM: Artificial
<220> FEATURE:
<223> OTHER INFORMATION: Synthetic polypeptide sequence of Streptomyces
      sp M23 CBH2 with NprM signal peptide and restriction site

<400> SEQUENCE: 2

```
Met Lys Lys Lys Lys Gln Ala Leu Lys Val Leu Leu Ser Val Gly Ile
1               5                   10                  15

Leu Ser Ser Ser Phe Ala Phe Ala His Thr Ser Ala Ala Thr Ser
            20                  25                  30

Met Gly Pro Ala Ala Pro Thr Ala Arg Val Asp Asn Pro Tyr Val Gly
        35                  40                  45

Ala Thr Met Tyr Val Asn Pro Glu Trp Ser Ala Leu Ala Ala Ser Glu
    50                  55                  60

Pro Gly Gly Asp Arg Val Ala Asp Gln Pro Thr Ala Val Trp Leu Asp
65                  70                  75                  80

Arg Ile Ala Thr Ile Glu Gly Val Asp Gly Lys Met Gly Leu Arg Glu
                85                  90                  95

His Leu Asp Glu Ala Leu Gln Gln Lys Gly Ser Gly Glu Leu Val Val
            100                 105                 110

Gln Leu Val Ile Tyr Asp Leu Pro Gly Arg Asp Cys Ala Ala Leu Ala
        115                 120                 125

Ser Asn Gly Glu Leu Gly Pro Asp Glu Leu Asp Arg Tyr Lys Ser Glu
    130                 135                 140

Tyr Ile Asp Pro Ile Ala Asp Ile Leu Ser Asp Ser Lys Tyr Glu Gly
145                 150                 155                 160

Leu Arg Ile Val Thr Val Ile Glu Pro Asp Ser Leu Pro Asn Leu Val
                165                 170                 175
```

```
Thr Asn Ala Gly Gly Thr Asp Thr Thr Thr Glu Ala Cys Thr Thr Met
            180                 185                 190

Lys Ala Asn Gly Asn Tyr Glu Lys Gly Val Ser Tyr Ala Leu Ser Lys
        195                 200                 205

Leu Gly Ala Ile Pro Asn Val Tyr Asn Tyr Ile Asp Ala Ala His His
        210                 215                 220

Gly Trp Leu Gly Trp Asp Thr Asn Leu Gly Pro Ser Val Gln Glu Phe
225                 230                 235                 240

Tyr Lys Val Ala Thr Ser Asn Gly Ala Ser Val Asp Asp Val Ala Gly
                245                 250                 255

Phe Ala Val Asn Thr Ala Asn Tyr Ser Pro Thr Val Glu Pro Tyr Phe
                260                 265                 270

Thr Val Ser Asp Thr Val Asn Gly Gln Thr Val Arg Gln Ser Lys Trp
            275                 280                 285

Val Asp Trp Asn Gln Tyr Val Asp Glu Gln Ser Tyr Ala Gln Ala Leu
        290                 295                 300

Arg Asn Glu Ala Val Ala Ala Gly Phe Asn Ser Asp Ile Gly Val Ile
305                 310                 315                 320

Ile Asp Thr Ser Arg Asn Gly Trp Gly Gly Ser Asp Arg Pro Ser Gly
                325                 330                 335

Pro Gly Pro Gln Thr Ser Val Asp Ala Tyr Val Asp Gly Ser Arg Ile
                340                 345                 350

Asp Arg Arg Val His Val Gly Asn Trp Cys Asn Gln Ser Gly Ala Gly
            355                 360                 365

Leu Gly Glu Arg Pro Thr Ala Ala Pro Ala Ser Gly Ile Asp Ala Tyr
        370                 375                 380

Thr Trp Ile Lys Pro Pro Gly Glu Ser Asp Gly Asn Ser Ala Pro Val
385                 390                 395                 400

Asp Asn Asp Glu Gly Lys Gly Phe Asp Gln Met Cys Asp Pro Ser Tyr
                405                 410                 415

Gln Gly Asn Ala Arg Asn Gly Tyr Asn Pro Ser Gly Ala Leu Pro Asp
                420                 425                 430

Ala Pro Leu Ser Gly Gln Trp Phe Ser Ala Gln Phe Arg Glu Leu Met
        435                 440                 445

Gln Asn Ala Tyr Pro Pro Leu Ser
        450                 455

<210> SEQ ID NO 3
<211> LENGTH: 1275
<212> TYPE: DNA
<213> ORGANISM: Artificial
<220> FEATURE:
<223> OTHER INFORMATION: Synthetic DNA codon optimized polynucleotide
      sequence encoding the mature form of the native Ssp CBH2

<400> SEQUENCE: 3
atggggcctg ctgcacctac tgcacgtgtg gataatcctt atgtaggcgc gacaatgtac     60
gtaaatccag aatggtcagc tcttgctgct tcggaaccag gtggtgatcg tgttgcagat    120
caacctacgg ctgtttggtt agatcgtatt gcaactattg aaggtgttga tggaaaaatg    180
ggattacgag aacatcttga tgaagcgtta aacaaaaag gaagcggaga acttgtggta    240
cagttagtaa tttatgattt acctggtcgt gattgcgcgg ctcttgctag taatggtgaa    300
ttaggtcctg atgaattaga tcgatataaa agcgaatata ttgatccgat tgcagacatt    360
ttatcggatt ccaaatatga aggacttcgt attgttacgg ttattgaacc agacagctta    420
```

```
cctaatttag taacaaacgc aggtggtaca gatacaacga cagaagcatg tactactatg    480
aaagcaaacg gtaattatga aaaggggta tcgtatgcgc tttctaaatt aggtgcaatt     540
ccgaacgtat acaactatat tgatgctgct catcatggat ggttaggatg ggacacaaat    600
ttagggccat ccgtacagga attttataaa gtggcaacat caaatggcgc atccgttgat    660
gatgtggcgg gatttgcagt caatacagct aattattcac ctactgtaga accttatttt    720
acggtttcag atacggtgaa tgggcagacg gtacgtcaat ctaaatgggt tgactggaat    780
caatacgtag atgaacaaag ttatgcgcag gctttacgaa acgaagctgt cgccgctgga    840
tttaatagcg atattggtgt gattattgat acatcccgaa atggatgggg tggttcagat    900
cgcccttcag ggcctggccc tcaaacttcc gtagatgctt atgtagatgg atcacgaatt    960
gatcgtcgcg ttcatgtagg aaattggtgt aatcagtctg gagcaggctt aggtgaaaga   1020
ccaacagcag caccagctag cgggattgat gcatatacat ggattaaacc gccgggcgaa   1080
tctgatggaa attcagctcc ggttgataat gacgaaggaa aaggatttga ccaaatgtgt   1140
gatcctagct accagggaaa cgctcgcaat ggctacaatc cttcaggagc gttacctgat   1200
gcaccattaa gtggacaatg gttttcggca caatttcgtg aattaatgca aaatgcatat   1260
cctccattat cttga                                                    1275
```

<210> SEQ ID NO 4
<211> LENGTH: 424
<212> TYPE: PRT
<213> ORGANISM: Artificial
<220> FEATURE:
<223> OTHER INFORMATION: Synthetic polypeptide sequence of the mature
      form of native Ssp M23 CBH2

<400> SEQUENCE: 4

```
Met Gly Pro Ala Ala Pro Thr Ala Arg Val Asp Asn Pro Tyr Val Gly
1               5                   10                  15

Ala Thr Met Tyr Val Asn Pro Glu Trp Ser Ala Leu Ala Ala Ser Glu
            20                  25                  30

Pro Gly Gly Asp Arg Val Ala Asp Gln Pro Thr Ala Val Trp Leu Asp
        35                  40                  45

Arg Ile Ala Thr Ile Glu Gly Val Asp Gly Lys Met Gly Leu Arg Glu
    50                  55                  60

His Leu Asp Glu Ala Leu Gln Gln Lys Gly Ser Gly Glu Leu Val Val
65                  70                  75                  80

Gln Leu Val Ile Tyr Asp Leu Pro Gly Arg Asp Cys Ala Ala Leu Ala
                85                  90                  95

Ser Asn Gly Glu Leu Gly Pro Asp Glu Leu Asp Arg Tyr Lys Ser Glu
            100                 105                 110

Tyr Ile Asp Pro Ile Ala Asp Ile Leu Ser Asp Ser Lys Tyr Glu Gly
        115                 120                 125

Leu Arg Ile Val Thr Val Ile Glu Pro Asp Ser Leu Pro Asn Leu Val
    130                 135                 140

Thr Asn Ala Gly Gly Thr Asp Thr Thr Thr Glu Ala Cys Thr Thr Met
145                 150                 155                 160

Lys Ala Asn Gly Asn Tyr Glu Lys Gly Val Ser Tyr Ala Leu Ser Lys
                165                 170                 175

Leu Gly Ala Ile Pro Asn Val Tyr Asn Tyr Ile Asp Ala Ala His His
            180                 185                 190

Gly Trp Leu Gly Trp Asp Thr Asn Leu Gly Pro Ser Val Gln Glu Phe
        195                 200                 205
```

```
Tyr Lys Val Ala Thr Ser Asn Gly Ala Ser Val Asp Asp Val Ala Gly
    210                 215                 220
Phe Ala Val Asn Thr Ala Asn Tyr Ser Pro Thr Val Glu Pro Tyr Phe
225                 230                 235                 240
Thr Val Ser Asp Thr Val Asn Gly Gln Thr Val Arg Gln Ser Lys Trp
                245                 250                 255
Val Asp Trp Asn Gln Tyr Val Asp Glu Gln Ser Tyr Ala Gln Ala Leu
            260                 265                 270
Arg Asn Glu Ala Val Ala Ala Gly Phe Asn Ser Asp Ile Gly Val Ile
        275                 280                 285
Ile Asp Thr Ser Arg Asn Gly Trp Gly Gly Ser Asp Arg Pro Ser Gly
    290                 295                 300
Pro Gly Pro Gln Thr Ser Val Asp Ala Tyr Val Asp Gly Ser Arg Ile
305                 310                 315                 320
Asp Arg Arg Val His Val Gly Asn Trp Cys Asn Gln Ser Gly Ala Gly
                325                 330                 335
Leu Gly Glu Arg Pro Thr Ala Ala Pro Ala Ser Gly Ile Asp Ala Tyr
            340                 345                 350
Thr Trp Ile Lys Pro Pro Gly Glu Ser Asp Gly Asn Ser Ala Pro Val
        355                 360                 365
Asp Asn Asp Glu Gly Lys Gly Phe Asp Gln Met Cys Asp Pro Ser Tyr
    370                 375                 380
Gln Gly Asn Ala Arg Asn Gly Tyr Asn Pro Ser Gly Ala Leu Pro Asp
385                 390                 395                 400
Ala Pro Leu Ser Gly Gln Trp Phe Ser Ala Gln Phe Arg Glu Leu Met
                405                 410                 415
Gln Asn Ala Tyr Pro Pro Leu Ser
            420

<210> SEQ ID NO 5
<211> LENGTH: 1275
<212> TYPE: DNA
<213> ORGANISM: Artificial
<220> FEATURE:
<223> OTHER INFORMATION: Synthetic DNA polynucleotide sequence encoding
      CBH2 variant No. 72

<400> SEQUENCE: 5
atggggcctg ctgcacctac tgcacgtgtg gataatcctt atgtaggcgc gacaatgtac      60
gtaaatccag aatggtcagc tcttgctgct tcggaaccag gtggtgatcg tgttgcagat     120
caacctacgg ctgtttggtt agatcgtatt gcaactattg aaggtgttga tggaaaaatg     180
ggattacgag aacatcttga tgaagcgtta aacaaaaag gaagcggaga acttgtggta     240
cagttagtaa tttatgattt acctggtcgt gattgcgcgg ctcttgctag taatggtgaa     300
ttaggtcctg atgaattaga tcgatataaa agcgaatata ttgatccgat tgcagacatt     360
ttatcggatt ccaaatatga aggacttcgt attgttacgg ttattgaacc agacagctta     420
cctaatttag taacaaacgc aggtggtaca gatacaacga cagaagcatg tactactatg     480
aaagcaaacg gtaattatga aaaggggta tcgtatgcgc tttctaaatt aggtgcaatt     540
ccgaacgtat acaactatat tgatgctgct catcatggat ggttaggatg ggacacaaat     600
tttgggccat ccgtacagga atttataaa gtggcaacat caaatggcgc atccgttgat     660
gatgtggcgg gatttgcagt caatacagct aattattcag caactgtaga accttatttt     720
acggtttcag atacggtgaa tgggcagacg gtacgtcaat ctaaatgggt tgactggaat     780
```

```
caatacgtag atgaacaaag ttatgcgcag gctttacgaa acgaagctgt cgccgctgga    840
tttaatagcg atattggtgt gattattgat acatcccgaa atggatgggg tggtccagat    900
cgcccttcag ggcctggccc tcaaacttcc gtagatgctt atgtagatgg atcacgaatt    960
gatcgtcgcg ttcatgtagg aaattggtgt aatcagtctg gagcaggctt aggtgaaaga   1020
ccaacagcag caccagctag cgggattgat gcatatacat ggattaaacc gccgggcgaa   1080
tctgatggaa attcagctcc ggttgataat gacgaaggaa aaggatttga ccgtatgtgt   1140
gatcctagct accagggaaa cgctcgcaat ggctacaatc cttcaggagc gttacctgat   1200
gcaccattaa gtggacaatg gttttcggca caatttcgtg aattaatgca aaatgcatat   1260
cctccattat cttga                                                   1275
```

<210> SEQ ID NO 6
<211> LENGTH: 424
<212> TYPE: PRT
<213> ORGANISM: Artificial
<220> FEATURE:
<223> OTHER INFORMATION: Synthetic polypeptide sequence of CBH2 variant
      No. 72

<400> SEQUENCE: 6

```
Met Gly Pro Ala Ala Pro Thr Ala Arg Val Asp Asn Pro Tyr Val Gly
1               5                  10                  15

Ala Thr Met Tyr Val Asn Pro Glu Trp Ser Ala Leu Ala Ala Ser Glu
            20                  25                  30

Pro Gly Gly Asp Arg Val Ala Asp Gln Pro Thr Ala Val Trp Leu Asp
        35                  40                  45

Arg Ile Ala Thr Ile Glu Gly Val Asp Gly Lys Met Gly Leu Arg Glu
    50                  55                  60

His Leu Asp Glu Ala Leu Gln Gln Lys Gly Ser Gly Glu Leu Val Val
65                  70                  75                  80

Gln Leu Val Ile Tyr Asp Leu Pro Gly Arg Asp Cys Ala Ala Leu Ala
                85                  90                  95

Ser Asn Gly Glu Leu Gly Pro Asp Glu Leu Asp Arg Tyr Lys Ser Glu
            100                 105                 110

Tyr Ile Asp Pro Ile Ala Asp Ile Leu Ser Asp Ser Lys Tyr Glu Gly
        115                 120                 125

Leu Arg Ile Val Thr Val Ile Glu Pro Asp Ser Leu Pro Asn Leu Val
    130                 135                 140

Thr Asn Ala Gly Gly Thr Asp Thr Thr Thr Glu Ala Cys Thr Thr Met
145                 150                 155                 160

Lys Ala Asn Gly Asn Tyr Glu Lys Gly Val Ser Tyr Ala Leu Ser Lys
                165                 170                 175

Leu Gly Ala Ile Pro Asn Val Tyr Asn Tyr Ile Asp Ala Ala His His
            180                 185                 190

Gly Trp Leu Gly Trp Asp Thr Asn Phe Gly Pro Ser Val Gln Glu Phe
        195                 200                 205

Tyr Lys Val Ala Thr Ser Asn Gly Ala Ser Val Asp Asp Val Ala Gly
    210                 215                 220

Phe Ala Val Asn Thr Ala Asn Tyr Ser Ala Thr Val Glu Pro Tyr Phe
225                 230                 235                 240

Thr Val Ser Asp Thr Val Asn Gly Gln Thr Val Arg Gln Ser Lys Trp
                245                 250                 255

Val Asp Trp Asn Gln Tyr Val Asp Glu Gln Ser Tyr Ala Gln Ala Leu
            260                 265                 270
```

```
Arg Asn Glu Ala Val Ala Ala Gly Phe Asn Ser Asp Ile Gly Val Ile
            275                 280                 285
Ile Asp Thr Ser Arg Asn Gly Trp Gly Gly Pro Asp Arg Pro Ser Gly
    290                 295                 300
Pro Gly Pro Gln Thr Ser Val Asp Ala Tyr Val Asp Gly Ser Arg Ile
305                 310                 315                 320
Asp Arg Arg Val His Val Gly Asn Trp Cys Asn Gln Ser Gly Ala Gly
                325                 330                 335
Leu Gly Glu Arg Pro Thr Ala Ala Pro Ala Ser Gly Ile Asp Ala Tyr
            340                 345                 350
Thr Trp Ile Lys Pro Pro Gly Glu Ser Asp Gly Asn Ser Ala Pro Val
            355                 360                 365
Asp Asn Asp Glu Gly Lys Gly Phe Asp Arg Met Cys Asp Pro Ser Tyr
    370                 375                 380
Gln Gly Asn Ala Arg Asn Gly Tyr Asn Pro Ser Gly Ala Leu Pro Asp
385                 390                 395                 400
Ala Pro Leu Ser Gly Gln Trp Phe Ser Ala Gln Phe Arg Glu Leu Met
                405                 410                 415
Gln Asn Ala Tyr Pro Pro Leu Ser
            420

<210> SEQ ID NO 7
<211> LENGTH: 1275
<212> TYPE: DNA
<213> ORGANISM: Artificial
<220> FEATURE:
<223> OTHER INFORMATION: Synthetic DNA polynucleotide sequence encoding
      CBH2 variant No. 90

<400> SEQUENCE: 7
atggggcctg ctgcacctac tgcacgtgtg gataatcctt atgtaggcgc gacaatgtac      60
gtaaatccag aatggtcagc tcttgctgct tcggaaccag gtggtgatcg tgttgcagat     120
caacctacgg ctgtttggtt agatcgtatt gcaactattg aaggtgttga tggaaaaatg     180
ggattacgag aacatcttga tgaagcgtta caacaaaaag aagcggagaa acttgtggta     240
cagttagtaa tttatgattt acctggtcgt gattgcgcgg ctcttgctag taatggtgaa     300
ttaggtcctg atgaattaga tcgatataaa gcgaatata  ttgatccgat tcgtgacatt     360
ttatcggatt ccaaatatga aggacttcgt attgttacgg ttattgaacc agacagctta     420
cctaatttag taacaaacgc aggtggtaca gatacaacga cagaagcatg tactactatg     480
aaagcaaacg gtaattatga aaaggggta  tcgtatgcgc tttctaaatt aggtgcaatt     540
ccgaacgtat acaactatat tgatgctgct catcatggat ggttaggatg gacacaaaat     600
tttgggccat ccgtacagga attttataaa gtggcaacat caaatggcgc atccgttgat     660
gatgtggcgg gatttgcagt caatacagct aattattcag caactgtaga acctatttt      720 acggtttcag atacggtgaa tgggcagacg gtacgtcaat ctaaatgggt tgactggaat     780
caatacgtag atgaacaaag ttatgcgcag gctttacgaa acgaagctgt cgccgctgga     840
tttaatagcg atattggtgt gattattgat acatcccgaa atggatgggg tggtccagat     900
cgcccttcag ggcctggccc tcaaacttcc gtagatgctt atgtagatgg atcacgaatt     960
gatcgtcgcg ttcatgtagg aaattggtgt aatcagtctg gagcaggctt aggtgaaaga    1020
ccaacagcag caccagctag cgggattgat gcatatacat ggattaaacc gccgggcgaa    1080
tctgatggaa attcagctcc ggttgataat gacgaaggaa aaggatttga ccgtatgtgt    1140
```

```
gatcctagct accagggaaa cgctcgcaat ggctacaatc ctaccggagc gttacctgat    1200
gcaccattaa gtggacaatg gttttcggca caatttcgtg aattaatgca aaatgcatat    1260
cctccattat cttga                                                    1275
```

<210> SEQ ID NO 8
<211> LENGTH: 424
<212> TYPE: PRT
<213> ORGANISM: Artificial
<220> FEATURE:
<223> OTHER INFORMATION: Synthetic polypeptide sequence of CBH2 variant
      No. 90

<400> SEQUENCE: 8

```
Met Gly Pro Ala Ala Pro Thr Ala Arg Val Asp Asn Pro Tyr Val Gly
1               5                   10                  15

Ala Thr Met Tyr Val Asn Pro Glu Trp Ser Ala Leu Ala Ala Ser Glu
            20                  25                  30

Pro Gly Gly Asp Arg Val Ala Asp Gln Pro Thr Ala Val Trp Leu Asp
        35                  40                  45

Arg Ile Ala Thr Ile Glu Gly Val Asp Gly Lys Met Gly Leu Arg Glu
    50                  55                  60

His Leu Asp Glu Ala Leu Gln Gln Lys Gly Ser Gly Glu Leu Val Val
65                  70                  75                  80

Gln Leu Val Ile Tyr Asp Leu Pro Gly Arg Asp Cys Ala Ala Leu Ala
                85                  90                  95

Ser Asn Gly Glu Leu Gly Pro Asp Glu Leu Asp Arg Tyr Lys Ser Glu
            100                 105                 110

Tyr Ile Asp Pro Ile Arg Asp Ile Leu Ser Asp Ser Lys Tyr Glu Gly
        115                 120                 125

Leu Arg Ile Val Thr Val Ile Glu Pro Asp Ser Leu Pro Asn Leu Val
    130                 135                 140

Thr Asn Ala Gly Gly Thr Asp Thr Thr Thr Glu Ala Cys Thr Thr Met
145                 150                 155                 160

Lys Ala Asn Gly Asn Tyr Glu Lys Gly Val Ser Tyr Ala Leu Ser Lys
                165                 170                 175

Leu Gly Ala Ile Pro Asn Val Tyr Asn Tyr Ile Asp Ala Ala His His
            180                 185                 190

Gly Trp Leu Gly Trp Asp Thr Asn Phe Gly Pro Ser Val Gln Glu Phe
        195                 200                 205

Tyr Lys Val Ala Thr Ser Asn Gly Ala Ser Val Asp Asp Val Ala Gly
    210                 215                 220

Phe Ala Val Asn Thr Ala Asn Tyr Ser Ala Thr Val Glu Pro Tyr Phe
225                 230                 235                 240

Thr Val Ser Asp Thr Val Asn Gly Gln Thr Val Arg Gln Ser Lys Trp
                245                 250                 255

Val Asp Trp Asn Gln Tyr Val Asp Glu Gln Ser Tyr Ala Gln Ala Leu
            260                 265                 270

Arg Asn Glu Ala Val Ala Ala Gly Phe Asn Ser Asp Ile Gly Val Ile
        275                 280                 285

Ile Asp Thr Ser Arg Asn Gly Trp Gly Gly Pro Asp Arg Pro Ser Gly
    290                 295                 300

Pro Gly Pro Gln Thr Ser Val Asp Ala Tyr Val Asp Gly Ser Arg Ile
305                 310                 315                 320

Asp Arg Arg Val His Val Gly Asn Trp Cys Asn Gln Ser Gly Ala Gly
                325                 330                 335
```

```
Leu Gly Glu Arg Pro Thr Ala Ala Pro Ala Ser Gly Ile Asp Ala Tyr
            340                 345                 350

Thr Trp Ile Lys Pro Pro Gly Glu Ser Asp Gly Asn Ser Ala Pro Val
        355                 360                 365

Asp Asn Asp Glu Gly Lys Gly Phe Asp Arg Met Cys Asp Pro Ser Tyr
        370             375             380

Gln Gly Asn Ala Arg Asn Gly Tyr Asn Pro Thr Gly Ala Leu Pro Asp
385             390             395                     400

Ala Pro Leu Ser Gly Gln Trp Phe Ser Ala Gln Phe Arg Glu Leu Met
                405             410                 415

Gln Asn Ala Tyr Pro Pro Leu Ser
            420
```

VARIANT CBH2 CELLULASES AND RELATED POLYNUCLEOTIDES

This application claims the benefit of provisional application U.S. Ser. No. 61/239,914, filed Sep. 4, 2009 pursuant to 35 U.S.C. §119(e) which is hereby incorporated by reference in its entirety.

FIELD OF THE INVENTION

The present invention relates, inter alia, to novel variant cellobiohydrolase (CBH) enzymes and isolated polynucleotides which encode polypeptides having cellobiohydrolase activity. The invention also relates to nucleic acid constructs, vectors and host cells comprising the polynucleotide sequences as well as methods for producing recombinant variant CBH polypeptides in host cells and methods for using the variant CBH enzymes in industrial applications.

REFERENCE TO SEQUENCE LISTING

The "Sequence Listing" submitted electronically concurrently herewith pursuant 37 C.F.R. §1.821 in a computer readable form (CRF) via EFS-Web as file name CX3-021WO1_ST25.txt is incorporated herein by reference. The electronic copy of the Sequence Listing was created on Aug. 23, 2010, and the size on disk is 22.6 Kbytes.

BACKGROUND OF THE INVENTION

Cellulosic biomass is a significant renewable resource for the generation of sugars. Fermentation of these sugars can yield numerous end-products such as fuels and chemicals, which are currently derived from petroleum. While the fermentation of sugars to fuels such as ethanol is relatively straightforward, the hydrolytic conversion of cellulosic biomass to fermentable sugars such as glucose is difficult because of the crystalline structure of cellulose and its close association with lignin (Ladisch, et al., 1983 *Enzyme Microb. Technol.* 5:82). Pretreatment, by means, including but not limited to, mechanical and solvent means, increases the susceptibility of cellulose to hydrolysis. Pretreatment may be followed by the enzymatic conversion of cellulose to glucose, cellobiose, cello-oligosaccharides and the like, using enzymes that specialize in breaking down the β-1-4 glycosidic bonds of cellulose. These enzymes are collectively referred to as "cellulases".

Cellulases may be divided into three major sub-categories of enzymes: 1,4-β-D-glucan glucanohydrolases ("endoglucanases" or "EGs"); 1,4-β-D-glucan cellobiohydrolases ("exoglucanases", "cellobiohydrolases", or "CBHs"); and β-D-glucoside-glucohydrolases ("β-glucosidases", "cellobiases" or "BGs"). Endoglucanases randomly attack the interior parts, and mainly the amorphous regions of cellulose, mostly yielding glucose, cellobiose, and cellotriose. Exoglucanases incrementally shorten the glucan molecules by binding to the glucan ends and releasing mainly cellobiose units from the ends of the cellulose polymer. β-glucosidases split the cellobiose, a water-soluble β-1,4-linked dimer of glucose, into two units of glucose. The cellulase enzyme classification can be further expanded to include multiple components within each cellulase classification. For example, numerous EGs, CBHs and BGs have been isolated from a variety of organisms such as *Trichoderma reesei* and *Humicola insolens*. It is known that *Trichoderma reesei* contain at least 8 EGS, including EGI, EGII, EGIII, EGIV, EGV, EGVI, EGVII and EGVIII; at least 5 BGs, including BG1, BG2, BG3, BG4, BG5 and at least 2 CBHs (CBH1 and CBH2) (Foreman P. K. *J. Biol. Chem.* 2003, 278:31988-31997).

Most CBHs are multi-domain proteins consisting of a catalytic domain and a cellulose or carbohydrate binding domain (CBD) separated by a linker region. The catalytic domain is responsible for cleavage of the cellulose. The catalytic domain is classified into the glycoside hydrolase family wherein the family members include enzymes having a similar fold and hydrolytic mechanisms. The CBH2s (Cel6) are members of the glycoside hydrolase Family 6. The three dimension structure of a number of CBHs is known. Generally CBH2 enzymes operate on the non-reducing end of a cellulase substrate as compared to CBH1 enzymes. In addition, there are a number of CBH2s which do not include a CBD.

The use of cellulase enzymes in various industrial applications is well known. Cellulases have been used in the treatment of textiles for the purpose of enhancing the cleaning ability of detergent compositions, for use as a softening agent for improving the feel and appearance of cotton fabrics; and for denim finishing (U.S. Pat. No. 5,648,263, U.S. Pat. No. 5,776,757, and Kumar et al., *Textile Chemist and Colorist* 1997, 29:37-4). Cellulases have also been used in the pulp and paper industry for treating fibers, in the food industry, and as an additive in animal feed. In addition, cellulases have been used in the saccharification process to hydrolyze carbon substrates (including both starch and cellulose), to fermentable sugars.

The production of fermentable sugars from renewable biomass substrates (e.g., lignocellulosic feedstocks) with the sequential or simultaneous production of fuel products and/or other chemical end-products to reduce dependence on fossil fuels has emerged as a worldwide recognized goal.

While cellulase compositions and modified cellulase enzymes have been previously described (US Patent Publication No. 20060205042 and US Patent Publication No. 20080076152) cellulases that exhibit improved performance characteristics such as but not limited to increased thermostability, improved stability, improved activity, and the like are of particular interest.

SUMMARY OF THE INVENTION

The present invention provides isolated cellulase proteins, identified herein as variant CBH2 polypeptides and the nucleic acids which encode the variant CBH2 polypeptides.

The invention relates to variant Family 6 cellulases produced by the substitution of at least one amino acid at a position selected from position T18, M19, L28, A30, S31, A51, T52, E64, E68, E77, D104, K110, A118, S122, S124, G128, D151, T153, E155, T158, T159, M160, S175, I180, V183, L201, G202, P203, Q206, G216, S218, V219, D220, D221, A226, S233, P234, T241, T245, Q253, K255, Q261, A269, A271, N274, A276, N282, V287, S299, S303, G304, S310, V311, D312, A313, V324, S347, P357, A366, V368, Q378, S383, Q385, and S395, wherein amino acid position is determined by optimal alignment with SEQ ID NO: 4.

The invention also relates to variant Family 6 cellulases which provide an improved cellulase with increased thermostability, increase stability, and/or increased tolerance to low pH levels (e.g., 4.0 to 5.5) as compared to the wild type or native *Streptomyces* sp M23 CBH2 (e.g., the CBH2 having SEQ ID NO: 4).

In one embodiment the invention pertains to an isolated variant CBH2 polypeptide comprising: (a) an amino acid sequence that is at least about 70% identical to wild type *Streptomyces* sp M23 CBH2 having SEQ ID NO: 4 and having at least one substitution or deletion of an amino acid residue corresponding to one or more positions of T18, M19, L28, A30, S31, A51, T52, E64, E68, E77, D104, K110, A118, S122, S124, G128, D151, T153, E155, T158, T159, M160, S175, I180, V183, L201, G202, P203, Q206, G216, S218, V219, D220, D221, A226, S233, P234, T241, T245, Q253, K255, Q261, A269, A271, N274, A276, N282, V287, S299, S303, G304, S310, V311, D312, A313, V324, S347, P357, A366, V368, Q378, S383, Q385, and S395, wherein amino acid position is determined by optimal alignment with SEQ ID NO: 4; (b) an amino acid sequence encoded by a nucleic acid that hybridizes under stringent conditions over substantially the entire length of a nucleic acid corresponding to a sequence selected from the group consisting of (i) SEQ ID NO: 3; or (ii) a complementary sequence of (i), wherein the encoded polypeptide has at least one or more substitutions or deletions at a position selected from the group consisting of T18, M19, L28, A30, S31, A51, T52, E64, E68, E77, D104, K110, A118, S122, S124, G128, D151, T153, E155, T158, T159, M160, S175, I180, V183, L201, G202, P203, Q206, G216, S218, V219, D220, D221, A226, S233, P234, T241, T245, Q253, K255, Q261, A269, A271, N274, A276, N282, V287, S299, S303, G304, S310, V311, D312, A313, V324, S347, P357, A366, V368, Q378, S383, Q385, and S395, wherein amino acid position is determined by optimal alignment with SEQ ID NO: 4 or (c) a variant CBH2 polypeptide fragment of (a) or (b).

In further embodiments of the invention an isolated variant CBH2 polypeptide includes an amino acid sequence comprising at least one substitution selected from the group of T18V, M19G, L28E, A30T, S31L, A51T, T52K/Y, E64G/A/K, E68G, E77P, D104A, K110R, A118R, S122V/H, S124P, G128D, D151E/T, T153V/P, E155P, T158A, T159R, M160Q, S175Q/L, I180K/C, V183I/G, L201R/F/M, G202F/Y, P203E, Q206L, G216K, S218V, V219E/R, D220Y, D221L, A226T, S233C, P234S/A, T241R/K, T245M, Q253M/A/S, K255R, Q261R, A269G, A271L, N274K/P, A276L/S, N282H, V287F, S299P, S303T, G304R, S310D, V311L, D312N, A313T, V324H/F, S347N, P357T, A366K, V368D, Q378R, S383T, Q385T/R and S395T, wherein amino acid position is determined by optimal alignment with SEQ ID NO: 4.

In some embodiments an isolated variant CBH2 polypeptide of the invention comprises an amino acid substitution selected from T18V, S31L, T52K/Y, E64A, D104A, S122V/H, D151E/T, T153V, T159R, M160Q, L201R/F/M, P234A/S, T241R, A276L and S383T, wherein amino acid position is determined by optimal alignment with SEQ ID NO: 4.

In one embodiment an isolated variant CBH2 polypeptide of the invention comprises at least 90% sequence identity to SEQ ID NO: 4 and comprises a substitution at position 201 (e.g., 201R, 201F or 201M). In some embodiments, the isolated variant CBH2 polypeptide having at least 90% sequence identity to SEQ ID NO: 4 and a substitution at position 201 further comprises a substitution at a position selected from 30, 118, 122, 175, 180, 183, 202, 206, 216, 219, 221, 233, 234, 241, 253, 274, 324, and 395 when aligned with SEQ ID NO: 4. In some embodiments the further substitutions are selected from A30T, A118R, S122V/H, S175Q/L, I180K/C, V183G, G202F/Y, Q206L, G216K, V219E/R, D221L, S233C, P234S/A, T241R/K, Q253M/A/S, N274K/P, V324H/F and S395T.

In one embodiment an isolated variant CBH2 polypeptide of the invention comprises an amino acid sequence that is at least 90% identical to SEQ ID NO: 4 and comprises a substitution at position 234 (e.g., 234A or 234S). In some embodiments the isolated variant CBH2 polypeptide of having at least 90% sequence identity to SEQ ID NO: 4 and a substitution at position 234 further comprises a substitution at a position selected from 77, 201, 271, and 378 when aligned with SEQ ID NO: 4. In some embodiments, the further substitutions are selected from the group of E77P, L201F, A271L, and Q378R.

The invention additionally pertains to a polynucleotide which encodes a variant CBH2 polypeptide encompassed by the invention as described herein. In further embodiments the invention relates to genetic constructs for directing expression and secretion of the variant CBH2 polypeptides encompassed by the invention. In some embodiments, the genetic construct is a vector comprising a polynucleotide encoding the variant CBH2 polypeptides, a DNA sequence regulating expression and secretion of the polypeptide such as but not limited to promoter sequences and signal sequences.

The present invention also relates to microbial host cells transformed with a genetic construct comprising a polynucleotide sequence encoding a variant CBH2 polypeptide of the invention. In some embodiments, the microbial host cell is a bacterial cell, a filamentous fungal cell or a yeast cell.

The present invention also relates to a method of producing a variant CBH2 polypeptide in a host cell comprising culturing a host cell transformed with a polynucleotide encoding a variant CBH2 polypeptide encompassed by the invention under suitable culture conditions to allow expression and production of the variant CBH2 polypeptide and obtaining the produced variant CBH2. In some embodiments, the variant CBH2 produced by the method is recovered from the culture and in other embodiments a composition comprising the cell culture which includes the variant CBH2 polypeptide is used in an industrial application.

The present invention also relates to enzyme compositions comprising a variant CBH2 polypeptide encompassed by the invention wherein the enzyme composition is used in (1) a process for saccharification of lignocellulosic or starch feedstocks for the production of fermentable sugars, fuel alcohols and/or other chemical end-products; (2) in a process of improving digestability of an animal feed; (3) in pulp and paper processing; and/or (4) in textile and detergent applications. In some embodiments the enzyme composition including the variant CBH2 polypeptide of the present invention will further include other cellulase enzymes (e.g., CBH1s, EGs, BGs and combinations thereof).

The above summary of the invention does not describe all features of the invention. The above features and other features of the invention will become more apparent from the following detailed description of the invention and description of the figures.

BRIEF DESCRIPTION OF THE FIGURES

FIG. 1A (SEQ ID NO: 1) depicts a polynucleotide sequence which encodes native *Streptomyces* sp M23 CBH2 ("Ssp CBH2"). The polynucleotide sequence has been codon optimized for expression in both *Bacillus megaterium* and *Escherichia coli*. The sequence includes the NprM signal peptide sequence (depicted in bold); part of the NprM cleavage site and an engineered SpeI restriction site (in italics and underlined); and the sequence encoding the Ssp CBH2 (1275 nucleotides).

FIG. 1B (SEQ ID NO: 2) depicts the amino acid encoded by the polynucleotide sequence of FIG. 1A and comprises the sequence encoding Ssp CBH2. The amino acid sequence includes the NprM signal peptide which is underlined. Cleavage of the signal peptide from the mature CBH2 occurs between residues 29 and 30 as indicated by the arrow. The amino acid residues at positions 31 and 32 respectively, are encoded by nucleotides that correspond to an engineered SpeI restriction site. These amino acid positions are in bold Amino acid residues 33 through 456 (MGPAA . . . ) encode the native Ssp (CBH2).

FIG. 2A (SEQ ID NO: 3) depicts a codon-optimized (for expression in both *Bacillus megaterium* and *E. coli*) polynucleotide sequence encoding the mature form of the native Ssp CBH2.

FIG. 2B (SEQ ID NO: 4) depicts the amino acid sequence of the mature form of the native Ssp M23 CBH2.

```
                                              (SEQ ID NO: 4)
MGPAAPTARVDNPYVGATMYVNPEWSALAASEPGGDRVADQP

TAVWLDRIATIEGVDGKMGLREHLDEALQQKGSGELVVQLVI

YDLPGRDCAALASNGELGPDELDRYKSEYIDPIADILSDSKY

EGLRIVTVIEPDSLPNLVTNAGGIDTTTEACTIMKANGNYEK

GVSYALSKLGAIPNVYNYIDAAHHGWLGWDTNLGPSVQEFYK

VATSNGASVDDVAGFAVNTANYSPTVEPYFTVSDIVNGQTVR

QSKWVDWNQYVDEQSYAQALRNEAVAAGFNSDIGVIIDTSRN

GWGGSDRPSGPGPQTSVDAYVDGSRIDRRVHVGNWCNQSGAG

LGERPTAAPASGIDAYTWIKPPGESDGNSAPVDNDEGKGFDQ

MCDPSYQGNARNGYNPSGALPDAPLSGQWFSAQFRELMQNAY

PPLS
```

FIGS. 3A-B illustrate the activity profile for Ssp CBH2 (solid line) and variant CBH2 polypeptides (sample no. 72, dashed lines and sample no. 90, dotted lines) over the time range of 96 hours using 200 g/L Avicel as a substrate and 0.2% enzyme load. The experimental procedure is more fully described in Example 7. FIG. 3A illustrates cellobiose yield (g/L) under pH 4.0 and 60° C., and FIG. 3B illustrates cellobiose yield (g/L) under pH 5.0 and 65° C. Error bars indicate ±1 standard deviation.

DETAILED DESCRIPTION OF THE INVENTION

All patent and publications, including any sequences disclosed herein within such patents or publications referred to herein are expressly incorporated by reference.

DEFINITIONS

Unless defined otherwise herein, all technical and scientific terms used herein have the same meaning as commonly understood by one of ordinary skill in the art to which the invention pertains. Singleton et al. Dictionary of Microbiology and Molecular Biology 3rd Ed., John Wiley and Sons, New York (2006) provides one of skill with a general dictionary of many of the terms used herein.

As used herein, the following terms are intended to have the following meanings.

The term "cellulase" refers to a category of enzymes capable of hydrolyzing cellulose (β-1,4-glucan or β-D-glucosidic linkages) to shorter oligosaccharides, cellobiose and/or glucose.

The term "exoglucanase", "cellobiohydrolase" or "CBH" refers to a group of cellulase enzymes classified as E.C. 3.2.1.91. These enzymes hydrolyze cellobiose from the reducing or non-reducing end of cellulose.

The term "CBH2" refers to a CBH that acts on the non-reducing end of cellulose polysaccharide chains, liberating either glucose or cellobiose.

A "CBH2 polypeptide" refers to a polypeptide having cellulase activity and specifically cellobiohydrolase activity.

The term "β-glucosidase" or "cellobiase" (E.C. 3.2.1.21) used interchangeably herein means a β-D-glucoside glucohydrolase which catalyzes the hydrolysis of a sugar dimer, including but not limited to cellobiose with the release of a corresponding sugar monomer.

"Cellulolytic activity" encompasses exoglucanase activity (CBH), endoglucanase (EG) activity and/or β-glucosidase activity.

The term "endoglucanase" or "EG" refers to a group of enzymes classified as E.C. 3.2.1.4. These enzymes hydrolyze internal β-1,4 glucosidic bonds of cellulose.

As used herein, the term "isolated" refers to a nucleic acid, polynucleotide, polypeptide, protein, or other component that is partially or completely separated from components with which it is normally associated (other proteins, nucleic acids, cells, synthetic reagents, etc.).

The term "wild type" as applied to a polypeptide (protein) means a polypeptide (protein) expressed by a naturally occurring microorganism such as bacteria or filamentous fungus found in nature. The term "native" as applied to a polypeptide (protein) means a polypeptide (protein) expressed by a naturally occurring microorganism such as bacteria or filamentous fungus found in nature that has been synthesized and/or codon optimized for expression in another host organism. The terms "wild type" and "native" may be used interchangeably herein.

A "variant" as used herein means a polypeptide which is derived from a precursor protein (e.g., the native or wild type protein) by addition of one or more amino acids to either or both the C- and N-terminal end, a substitution of one or more amino acids at one or more different sites in the amino acid sequence, or deletion of one or more amino acids at one or more amino acids at either or both ends of the protein or at one or more sites in the amino acid sequence. A CBH2 polypeptide variant of the invention retains the characteristic cellulolytic nature of the precursor enzyme but may have altered properties in some specific aspect. For example a CBH2 polypeptide variant may have an increased or decreased pH optimum or increased temperature or oxidative stability but will retain it characteristic celluloytic activity.

A "reference CBH2 sequence" refers to a defined sequence used as a basis for a sequence comparison. A reference CBH2 sequence may be a subset of a larger sequence. Generally a reference sequence is at least 50 amino acid residues in length, at least 100 residues in length, at least 150 residues in length at least 200 residues in length, at least 300 residues in length, at least 350 residues in length or the full length of the polypeptide. For instance, a reference sequence based on SEQ ID NO: 4 having at the residue corresponding to E64 a G (glycine) refers to a reference sequence in which the corresponding residue at E64 in SEQ ID NO: 4 has been changed to a G (glycine).

A nucleic acid (such as a polynucleotide) or a polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An "improved property" refers to a CBH2 polypeptide that exhibits an improvement in any property as compared to the Ssp CBH2 (SEQ ID NO: 4). Properties which may be improved include protein expression, thermo stability, pH activity, pH stability, product specificity, specific activity, substrate specificity, resistance to substrate or end-product inhibition, temperature profile, and chemical stability.

The term "improved thermoactivity" as used herein means a variant displaying an increase in the rate of hydrolysis and at the same time decreasing the time required and/or decreasing the amount of enzyme concentration required for hydrolysis as compared to the native enzyme or reference sequence when exposed to essentially the same conditions. Alternatively a variant with a reduced thermoactivity will catalyze a hydrolysis reaction at a temperature lower than the temperature optimum of the parent or reference as defined by the temperature dependent activity profile of the parent or reference.

The terms "percent identity," "% identity," "percent identical," and "% identical" are used interchangeably herein to refer to the percent amino acid sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art. See e.g., Dayhoff et al. (1978), "A model of evolutionary change in proteins"; "Atlas of Protein Sequence and Structure," Vol. 5, Suppl. 3 (Ed. M. O. Dayhoff), pp. 345-352, *Natl. Biomed. Res. Round.*, Washington, D.C.; and Henikoff et al. (1992) *Proc. Natl. Acad. Sci. USA*, 89:10915-10919, both of which are incorporated herein by reference. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul, et al. (1997) *Nucleic Acids Res.*, 25:3389-3402 (incorporated herein by reference), and made available to the public at the National Center for Biotechnology Information Website. Optimal alignments, including multiple alignments can be prepared using readily available programs such as PSI-BLAST, which is described by Altschul, et al. (1997) *Nucleic Acids Res.*, 25:3389-3402 and which is incorporated herein by reference.

"Corresponding to", "reference to" "or relative to" when used in the context of the numbering of a given amino acid or polynucleotide sequence refers to the numbering of the residues of a specified reference sequence when the given amino acid or polynucleotide sequence is compared to the reference sequence.

The "position" is denoted by a number that sequentially identifies each amino acid in the reference sequence based on its position relative to the N-terminus Owing to deletions, insertions, truncations, fusions, and the like that must be taken into account when determining an optimal alignment, in general the amino acid residue number in a test sequence determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen (1993) "Laboratory Techniques in Biochemistry and Molecular Biology-Hybridization with Nucleic Acid Probes," Part I, Chapter 2 (Elsevier, N.Y.), which is incorporated herein by reference.

For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

In describing the various variants of the present invention, the nomenclature described below is adapted for ease of reference. In all cases the accepted IUPAC single letter or triple letter amino acid abbreviations are employed. For amino acid substitutions the following nomenclature is used: Original amino acid, position, substituted amino acid. Accordingly the substitution of serine with glycine at position 34 is designated "Ser31Gly" or "S31G". A deletion is represented by "–". Thus, for example, "Ser31–" or "S31–" refers to a deletion at position 31.

The term "culturing" or "cultivation" refers to growing a population of microbial cells under suitable conditions in a liquid or solid medium. In some embodiments, culturing refers to fermentative bioconversion of a substrate (such as a cellulosic or starch containing substrate) to an end-product.

The term "contacting" refers to the placing of a respective enzyme in sufficiently close proximity to a respective substrate to enable the enzyme to convert the substrate to a product. Those skilled in the art will recognize that mixing a solution of the enzyme with the respective substrate will effect contacting.

The term "fermentable sugar" means simple sugars (monosaccharides, disaccharides and short oligosaccharides) such as but not limited to glucose, xylose, galactose, arabinose, mannose and sucrose. The term "soluble sugars" is used herein interchangeably with fermentable sugars.

As used herein, the term "fermentation" is used broadly to refer to the cultivation of a microorganism(s) that use simple sugars, such as fermentable or soluble sugars, as an energy source to obtain a desired product.

As used herein the term "transformed" or "transformation" used in reference to a cell means a cell has a non-native nucleic acid sequence integrated into its genome or as an episomal plasmid that is maintained through multiple generations.

As used herein "a", "an", and "the" include plural references unless the context clearly dictates otherwise.

The term "comprising" and its cognates are used in their inclusive sense; that is, equivalent to the term "including" and its corresponding cognates.

The term "introduced" in the context of inserting a nucleic acid sequence into a cell means transfected, transduced or transformed (collectively "transformed").

CBH2 Polypeptide Variants

The present invention provides novel variants of CBH2 polypeptides. In some preferred embodiments the enzymes are variants of a native Streptomyces sp. M23 CBH2 (Ssp CBH2) polypeptide. The present invention further includes variant CBH2 polypeptides that exhibit greater cellulase activity as compared to Ssp CBH2. Also included are variant CBH2 polypeptides that exhibit greater stability under conditions relevant to commercial saccharification processes as compared to a native Ssp CBH2 polypeptide.

More specifically, the invention relates to variant Family 6 cellulases produced by the substitution of at least one amino acid at a position selected from position T18, M19, L28, A30, S31, A51, T52, E64, E68, E77, D104, K110, A118, S122, S124, G128, D151, T153, E155, T158, T159, M160, S175, I180, V183, L201, G202, P203, Q206, G216, S218, V219, D220, D221, A226, S233, P234, T241, T245, Q253, K255, Q261, A269, A271, N274, A276, N282, V287, S299, S303, G304, S310, V311, D312, A313, V324, S347, P357, A366, V368, Q378, S383, Q385, and S395, wherein amino acid position is determined by optimal alignment with SEQ ID NO: 4. In addition to the CBH2 derived from Streptomyces sp M23, other non-limiting examples of Family 6 cellulases which may be modified according to the invention may be found in other species of Streptomyces (e.g., S. lividans, S. avermitilis, S. coelicolor, S. griseus, S. pristinaespiralis, S. sviceus), and further in species of Cellulomonas, Humicola, Phanerochaete, Pyromyces, Stackebrandtia, Thermobifida, Thermomonospora, and Trichoderma.

In one embodiment the invention pertains to an isolated CBH2 polypeptide variant comprising: (a) an amino acid sequence that is at least about 70% identical to wild type Streptomyces sp M23 CBH2 having SEQ ID NO: 4 and having at least one substitution or deletion of an amino acid residue corresponding to one or more positions of T18, M19, L28, A30, S31, A51, T52, E64, E68, E77, D104, K110, A118, S122, S124, G128, D151, T153, E155, T158, T159, M160, S175, I180, V183, L201, G202, P203, Q206, G216, S218, V219, D220, D221, A226, S233, P234, T241, T245, Q253, K255, Q261, A269, A271, N274, A276, N282, V287, S299, S303, G304, S310, V311, D312, A313, V324, S347, P357, A366, V368, Q378, S383, Q385, and/or S395, wherein amino acid position is determined by optimal alignment with SEQ ID NO: 4.

In some embodiments, the variant CBH2 polypeptides will comprise any number of combinations of substitutions listed above including combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or more of the above-identified positions up to a combination of substitutions at 55 positions. In some embodiments, the variant CBH2 polypeptides according to the invention will comprise between 2 and 15 combinations of substitutions.

In some embodiments, CBH2 polypeptide variants encompassed by the invention include those having an amino acid sequence that is at least about 75% identical to SEQ ID NO: 4 and having one or more of the above-identified substitutions. Certain of these CBH2 variants may be at least about 78% identical, at least about 80% identical, at least about 82% identical, at least about 85% identical, at least about 87% identical, at least about 88% identical, at least about 90% identical, at least about 91% identical, at least about 92% identical, at least about 93% identical, at least about 94% identical, at least about 95% identical, at least about 96% identical, at least about 97% identical, at least about 98% identical, at least about 99% identical to SEQ ID NO: 4. In some embodiments, the variant CBH2 polypeptides of the invention include those having an amino acid sequence that is at least 90% identical to SEQ ID NO: 4 and between 2 and 10 combinations of substitutions as compared to SEQ ID NO: 4.

The amino acid sequence comprising at least one substitution may be further selected from the group of T18V, M19G, L28E, A30T, S31L, A51T, T52K/Y, E64G/A/K, E68G, E77P, D104A, K110R, A118R, S122V/H, S124P, G128D, D151E/T, T153V/P, E155P, T158A, T159R, M160Q, S175Q/L, I180K/C, V183I/G, L201R/F/M, G202F/Y, P203E, Q206L, G216K, S218V, V219E/R, D220Y, D221L, A226T, S233C, P234S/A, T241R/K, T245M, Q253M/A/S, K255R, Q261R, A269G, A271L, N274K/P, A276L/S, N282H, V287F, S299P, S303T, G304R, S310D, V311L, D312N, A313T, V324H/F, S347N, P357T, A366K, V368D, Q378R, S383T, Q385T/R and/or S395T, wherein amino acid position is determined by optimal alignment with SEQ ID NO:4.

In some embodiments, an isolated CBH2 polypeptide variant of the invention comprises an amino acid sequence having at least 90% sequence identity (e.g., at least 90%, at least 93%, at least 95%, at least 97%, and at least 98%) to SEQ ID NO: 4 and at least one substitution of an amino acid residue selected from position T18, S31, T52, E64, D104, S122, D151, T153, T159, M160, L201, P234, T241, A276 and/or S383, wherein amino acid position is determined by optimal alignment with SEQ ID NO: 4. In some embodiments, the CBH2 variant will have at least 93% sequence identity to SEQ ID NO: 4 and have the substitution T18V, S31L, T52K/Y, E64A, D104A, S122V/H, D151E/T, T153V, T159R, M160Q, L201R/F/M, P234A/S, T241R, A276L or S383T, wherein amino acid position is determined by optimal alignment with SEQ ID NO: 4.

In one embodiment, an isolated CBH2 polypeptide variant of the invention comprises at least 90% sequence identity (e.g., at least 91%, 92%, 93%, 94%, 95%, 96%, 97%, 98% and 99%) to SEQ ID NO: 4 and comprises a substitution at position 201 when aligned with SEQ ID NO: 4. The substitution may be any substitution that imparts an altered activity or improved activity on the CBH2 variant as compared to the same activity of the wild type cellulase (SEQ ID NO: 4) under essentially the same conditions. Certain substitutions include L201R, L201F or L201M. In some embodiments, the isolated CBH2 polypeptide variant having a substitution at position 201 further comprises a substitution at a position selected from 30, 118, 122, 175, 180, 183, 202, 206, 216, 219, 221, 233, 234, 241, 253, 274, 324, and 395 when aligned with SEQ ID NO: 4. In some embodiments, the CBH2 variant will comprise at least 90% sequence identity to SEQ ID NO: 4, a substitution at position 201 and one additional position. In other embodiments the additional substitution will include at least two or at least 3 additional positions. In some embodiments, the substitution is selected from A30T, A118R, S122V/H, S175Q/L, I180K/C, V183G, G202F/Y, Q206L, G216K, V219E/R, D221L, S233C, P234S/A, T241R/K, Q253M/A/S, N274K/P, V324H/F and S395T. In some embodiments, the CBH2 variant of the invention will be selected from the group of V183G+L201F; K110R+L201F+Q385T; T159R+L201R+S383T; L201F+P234A+S383T; L201F+P234A; L201F+G202F; L201F+T241K; L201F+G202Y; L201F+S395T; A30T+L201F; A118R+L201F; S122V+L201F; S122H+ L201F; S175Q+L201F; S175L+L201F; L201F+Q206L; L201F+V219E; L201F+V219R; L201F+Q253M; L201F+Q253A; L201F+Q253S; I180K+L201F; I180C+L201F; L201F+G216K; L201F+D221L; L201F+S233C; L201F+V324H; L201F+N282H+V324F; L201F+N274K; and L201F+A276S+A366K.

In one embodiment, an isolated CBH2 polypeptide variant of the invention comprises an amino acid sequence that is at least 90% (e.g., at least 91%, 92%, 93%, 94%, 95%, 96%, 97%, 98% and 99%) identical to SEQ ID NO: 4 and comprises a substitution at position 234 when aligned with SEQ ID NO: 4. The substitution may be any substitution that imparts an altered activity or improved activity on the CBH2 variant as compared to the same activity of the wild type sequence (SEQ ID NO: 4) under essentially the same conditions. Certain substitutions include P234A and P234S. In some embodiments, the isolated CBH2 polypeptide variant having a substitution at position 234 further comprises a substitution at a position selected from 77, 201, 271, and 378 when aligned with SEQ ID NO: 4. In some embodiments, the variant will include at least 1 further substitution, at least 2, or at least 3 further substitutions. The CBH2 variant having at least one substitution at position 234 may further include a substitution selected from the group of E77P, L201F, A271L, and Q378R.

The present invention further provides an isolated and/or recombinant cellulase polypeptide variant having an amino acid sequence encoded by a nucleic acid that hybridizes under stringent conditions over substantially the entire length of a nucleic acid corresponding to a sequence selected from the group consisting of (i) SEQ ID NO: 3 (FIG. 2); or (ii) a complementary sequence of (i), wherein the encoded polypeptide has at least one or more substitutions or deletions at a position selected from the group of T18, M19, L28, A30, S31, A51, T52, E64, E68, E77, D104, K110, A118, S122, S124, G128, D151, T153, E155, T158, T159, M160, S175, I180, V183, L201, G202, P203, Q206, G216, S218, V219, D220, D221, A226, S233, P234, T241, T245, Q253, K255, Q261, A269, A271, N274, A276, N282, V287, S299, S303, G304, S310, V311, D312, A313, V324, S347, P357, A366, V368, Q378, S383, Q385, and S395, wherein amino acid position is determined by optimal alignment with SEQ ID NO: 4.

Variants of the present invention may comprise any of the following exemplary combinations of substitutions relative to SEQ ID NO: 4 or a sequence having at least 90% sequence identity (e.g., at least 93%, 95%, 96%, 97%, or 98%) to SEQ ID NO: 4, E64G+S218V; L28E+S310D+D312N+A313T+S383T+Q385T; E155P+T158A; L28E+S31L; S124P+G128D+A276L; A276L+S383T; E77P+P234A+S299P+Q378R; E64K+P234A+Q378R; P234A+S299P+Q378R; S299P+Q378R; P234A+Q378R; E64K+E77P+P234A+S299P+Q378R; E77P+P234A+Q378R; E64K+P234A+S299P+Q378R; E77P+P234A+V287F+S299P+Q378R; V287F+S299P+V311L; P234A+V287F+V311L; E77P+P234A+S299P+V311L+Q378R; E77P+P234A+S299P+G304R; E77P+P234A; P357T+Q378R; P234A+A271L; A51T+T159R+L201F+P234A+D312N+S383T; M19G+T159R+L201R+S383T; M19G+T159R+L201F+D312N+Q385T; M19G+L201F+N274P+D312N+Q385T; M19G+S31L+L201F+P234S+Q261R+D312N+S383T; V183G+L201F; S31L+T159R+L201F+S299P+S303T+A313T; S31L+T159R+L201R+P234A+T245M+S383T+Q385T; T159R+L201F+P234S+S383T+Q385T; K110R+L201F+Q385T; T159R+L201F+P234S+K255R+Q385T; A226T+P234S+V368D; T159R+L201R+D312N+Q385T; M19G+S31L+T159R+L201F+P234S+D312N; T159R+L201R+S383T; S31L+V183I+L201F+P234S+Q385T; E68G+L201F+P234A+D312N+S383T+Q385T; T159R+L201F+S383T+Q385T; L201F+P234A+S383T; M19G+L201F+P234S+S383T+Q385T; L201F+P234A; M19G+T159R+L201F+P234A+A269G+S347N+Q385T; L201F+G202F; L201F+T241K; L201F+G202Y; L201F+S235T; A30T+L201F; A118R+L201F; S122V+L201F; S122H+L201F; L201F+P234A+S299P+Q378R; S175Q+L201F; S175L+L201F; L201F+Q206L; L201F+V219E; L201F+V219R; L201F+Q253M; L201F+Q253A; L201F+Q2535; I180K+L201F; I180C+L201F; L201F+G216K; L201F+D221L; L201F+S233C; L201F+V324H; L201F+N282H+ V324F; L201F+N274K; L201F+A276S+A366K; A118R+L201F+P234A+S299P+Q378R+S395T; S122H+L201F+P203E+P234A+T241K+S299P+Q378R+S395T; A118R+S122V+S175Q+L201F+P234A+T241K+S299P+Q378R+S395T; L201F+D220Y+P234A+S289P+Q378R+S395T; S122V+L201F+P234A+T241K+S299P+Q378R+S395T; L201F+G202Y+P203E+D220Y+P234A+S299P+Q378R+S395T; A118R+S175Q+L201F+D220Y+P234A+T241K+S299P+Q378R+S395T; or A118R+L201F+G202F+P234A+S299P+Q378R+S395T.

Sequence-activity analyses indicated that certain of the above-described mutations (substitutions/deletions) appear particularly favorable with respect to improving CBH2 activity under certain conditions relative to native Ssp CBH2 (SEQ ID NO: 4). Sequence-activity analysis was performed in accordance with the methods described in WO 03/075129, U.S. Ser. No. 10/379,378 filed Mar. 3, 2003, and R. Fox et al., "Optimizing the search algorithm for protein engineering by directed evolution," *Protein Eng.* 16(8):589-597 (2003), both of which are incorporated herein by reference. See also R. Fox et al., "Directed molecular evolution by machine learning and the influence of nonlinear interactions," *J. Theor. Biol.* 234(2):187-199 (2005), which is incorporated herein by reference.

In accordance with the present invention, CBH2 activity can be determined by methods known in the art. Preferred assays for determining activity include the assays of Examples 6 through 8 for CBH2 activity using Avicel, PASC or biomass (e.g., wheat straw, bagasse or pretreated corn stover (PCS) as a substrate. In addition, assays for CBH2 expression include Western blot for the CBH2 protein, Northern blot analysis and reverse transcriptase polymerase chain reaction of cbh2 mRNA.

Improved Activities:

In some embodiments, CBH2 polypeptide variants of the present invention include those having improved (e.g., greater) cellulase activity relative to native *Streptomyces* sp. CBH2 (SEQ ID NO: 4) Improved activity may be measured by the assays described in either Examples 6, 7 or 8. For example, variant polypeptides of the present invention often have cellulase activity that is at least about 1-fold, at least about 2-fold, at least about 3-fold, and also at least about 4-fold or greater cellulase activity as compared to native (SEQ ID NO: 4), as measured for example in the assays described in either Examples 6, 7 or 8. Exemplary cellulase polypeptide variants having improved cellulase activity relative to native are identified in Table 2 of Example 9.

Exemplary variants according to the invention are represented by a) Sample No. 72 (Table 2, SEQ ID NO: 6) or b) sequences having at least 90% (e.g. at least 92%, 93%, 94%, 95%, 96%, 97%, 98% and 99%) sequence identity to SEQ ID NO: 6 and having at least one (e.g., at least 1, 2, 3, 4, 5, 6, 7, 8, 9 or 10) further substitutions, wherein SEQ ID NO: 6 is illustrated below.

```
                                            (SEQ ID NO: 6)
MGPAAPTARVDNPYVGATMYVNPEWSALAASEPGGDRVADQP

TAVWLDRIATIEGVDGKMGLREHLDEALQQKGSGELVVQLVI

YDLPGRDCAALASNGELGPDELDRYKSEYIDPIADILSDSKY

EGLRIVTVIEPDSLPNLVTNAGGIDTTTEACTIMKANGNYEK

GVSYALSKLGAIPNVYNYIDAAHHGWLGWDTNFGPSVQEFYK

VATSNGASVDDVAGFAVNTANYSATVEPYFTVSDTVNGQTVR

QSKWVDWNQYVDEQSYAQALRNEAVAAGFNSDIGVIIDTSRN

GWGGPDRPSGPGPQTSVDAYVDGSRIDRRVHVGNWCNQSGAG

LGERPTAAPASGIDAYTWIKPPGESDGNSAPVDNDEGKGFDR

MCDPSYQGNARNGYNPSGALPDAPLSGQWFSAQFRELMQNAY

PPLS.
```

In some embodiments of the invention, the variant CBH2 will comprise a sequence having at least 95% (e.g., 96%, 97%, 98%, and 99%) sequence identity to SEQ ID NO: 6 and 1 to 5 further amino acid substitutions when compared to SEQ ID NO: 6. In some embodiments, a variant CBH2 having at least 95% sequence identity to SEQ ID NO: 6, will be encoded by a polynucleotide sequence having at least 90% (e.g., 93%, 95%, 96%, 97%, 98%, 99% or even 100%) sequence identity to the polynucleotide sequence of SEQ ID NO: 5.

Other exemplary variants according to the invention are represented by a) Sample No. 90 (Table 2, SEQ ID NO: 8) or b) sequences having at least 90% (e.g. at least 92%, 93%, 94%, 95%, 96%, 97%, 98% and 99%) sequence identity to SEQ ID NO: 8 and at least one (e.g., at least 1, 2, 3, 4, 5, 6, 7, 8, 9 or 10) further substitutions, wherein SEQ ID NO: 8 is illustrated below.

```
                                            (SEQ ID NO: 8)
MGPAAPTARVDNPYVGATMYVNPEWSALAASEPGGDRVADQP

TAVWLDRIATIEGVDGKMGLREHLDEALQQKGSGELVVQLVI

YDLPGRDCAALASNGELGPDELDRYKSEYIDPIRDILSDSKY

EGLRIVTVIEPDSLPNLVTNAGGTDTTTEACTTMKANGNYEK

GVSYALSKLGAIPNVYNYIDAAHHGWLGWDTNFGPSVQEFYK

VATSNGASVDDVAGFAVNTANYSATVEPYFTVSDTVNGQTVR

QSKWVDWNQYVDEQSYAQALRNEAVAAGFNSDIGVIIDTSRN

GWGGPDRPSGPGPQTSVDAYVDGSRIDRRVHVGNWCNQSGAG

LGERPTAAPASGIDAYTWIKPPGESDGNSAPVDNDEGKGFDR

MCDPSYQGNARNGYNPTGALPDAPLSGQWFSAQFRELMQNAY

PPLS.
```

In some embodiments, the variants of the invention having cellulase activity will have at least 90% (at least 91%, at least 92%, at least 93%, at least 94%, at least 95%, at least 96%, at least 97%, at least 98%, at last 99% and even 100% sequence identity to SEQ ID NO: 8. In some embodiments, a variant CBH2 having at least 90% sequence identity to SEQ ID NO: 8, will be encoded by a polynucleotide sequence having at least 90% (e.g., 93%, 95%, 96%, 97%, 98%, 99% or even 100%) sequence identity to the polynucleotide sequence of SEQ ID NO: 7.

In some embodiments a CBH2 polypeptide variant of the invention will comprise a substitution of one or more amino acids at a position corresponding to position S122; S175; G202; P203; D220; and T241 when optimally aligned with SEQ ID NO: 8. In some embodiments, the substitution will include S122H/V; S175Q; G202F; P203E; D220Y; and T241K.

The variants of the present invention will, in some instances, produce at least about 1 times up to at least about 6 times more cellobiose as compared to the amount of cellobiose produced from the hydrolysis of Avicel or a biomass substrate by the native CBH2 (SEQ ID NO: 4) when exposed to substantially the same conditions.

In another embodiment, the present invention also provides a fragment of the CBH2 polypeptide variants described herein having cellulase activity. These fragments are referred to herein as "CBH2 fragments". As used herein, the term "fragment" refers to a polypeptide having a deletion of from 1 to 25 amino acid residues from the carboxy (C-)terminus, the amino (N-)terminus, or both (i.e., a deletion of 1, 2, 3, 4, 5, 6, 7, 8, 9, 10, 12, 13, 14, 15, 16, 17, 18, 19, 20, 21, 22, 23, 24, or 25 amino acid residues from either or both the N- or C-terminus). In some embodiments, the deletion may be from 1 to 20, or 1 to 15, or 1 to 10 residues, or 1 to 5 residues from the C-terminus, the N-terminus, or both. Particularly useful variants include those having C-terminal truncations. C-terminally truncated CBH2 variants may further have any one or combination of 2, 3, 4, 5, 6, 7, 8, 9, 10 or more of the substitutions described herein.

The present invention also provides CBH2 polypeptide variants having improved thermoactivity, improved thermostability, and/or improved stability at low and high pHs relative to native Ssp CBH2 (SEQ ID NO: 4). Variants of the present invention may exhibit an increase in residual activity. Residual activity is defined as the percentage activity retained after challenging an enzyme under stress conditions (for example, at pH 4.0 at 60° C.) for various times (for example, 8, 60 or 360 minutes) as compared to an unchallenged enzyme sample (t=0) of the same enzyme type. For example, the equation $$\% \text{ Residual Activity} = \frac{Activity_{(t=8,60,\ or\ 360\ minutes)}}{Activity_{(t=0)}} \times 100$$

is illustrative. In some embodiments, the % residual activity of a variant encompassed by the invention is at least 2×, 4×, 6×, 8×, 10×, 15×, 20×, 25×, 30×, 40×, 50×, 60×, 80× and even 100× greater than the % residual activity measured for the native Ssp CBH2 (SEQ ID NO: 4) under essentially the same conditions such as time, pH, temperature and the like. In some embodiments, a variant CBH2 will have an increase in residual activity that is at least 4× greater than the native Ssp CBH2 at a pH 5.0 at 60° C. or more (such as for example 65° C. or 70° C.) for about 6 hours or more (such as for example, at least 6 hours, at least 12 hours or at least 24 hours). In some embodiments, a variant CBH2 will have an increase in residual activity that is at least 10× greater than the native Ssp CBH2 at a pH 4.0 at 60° C. or more (such as for example at least 65° C. or at least 70° C.) for about 6 hours or more (such as for example at least 6 hours, at least 12 hours or at least 24 hours).

Variants of the present invention may exhibit a half life at a pH of about 6 or less (such as, for example, about 5.5, about 5, about 4.5 etc.) and a temperature of about 60° C. or more (such as, for example, 65° C., 70° C., 75° C., 80° C., etc.) of at least about 24 hours, at least about 36 hours, at least about 48 hours, up to at least about 72 hours or more as measured using the assay of Example 10. CBH2 variants of the present invention may exhibit a half life at a pH of about 8 or more (such as, for example, about 8.5, about 9, etc.) and a temperature of about 60° C. or more (such as, for example, 65° C., 70° C., etc.) of at least about 24 hours, at least about 36 hours, at least about 48 hours, up to at least about 72 hours or more as measured using the assay of Example 10.

The present invention includes conservatively modified variants of the CBH2 variants described herein. These variants have conservative substitutions made in their amino acid sequences. Examples of conservative substitutions are within the group of basic amino acids (arginine, lysine and histidine), acidic amino acids (glutamic acid and aspartic acid), polar amino acids (glutamine and asparagines), hydrophobic amino acids (leucine, isoleucine and valine), aromatic amino acids (phenylalanine, tryptophan and tyrosine), and small amino acids (glycine, alanine, serine, threonine, proline, cysteine and methionine) Amino acid substitutions that do not generally alter the specific activity are known in the art and are described, for example, by H. Neurath and R. L. Hill, 1979, in "The Proteins," Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Conservatively substituted variations of the polypeptide variants of the present invention include substitutions of a small percentage, typically less than 5%, more typically less than 2%, and often less than 1% of the amino acids of the polypeptide sequence, with a conservatively selected amino acid of the same conservative substitution group. In some embodiments, the conservatively substituted variations will include less than 20 amino acid positions, also less than 15, less than 10, less than 8, less than 5 amino acid, and less than 2 amino acid positions. The addition of sequences which do not alter the encoded activity of a CBH2, such as the addition of a non-functional or non-coding sequence, is considered a conservative variation of the CBH2 polynucleotide.

The amino acid and polynucleotide sequences of CBH2 polypeptides not specifically described herein can be readily generated and identified using methods that are well known to those having ordinary skill in the art. Libraries of these polypeptide variants may be generated and screened using the high throughput screen for presence of cellulase activity described in Example 8.

Methods for generating variant libraries are well known in the art. For example, mutagenesis and directed evolution methods can be readily applied to polynucleotides (such as, for example, native *Streptomyces* sp CBH2 encoding polynucleotides (e.g., SEQ ID NO: 3, FIG. 2) or the polynucleotides of the present invention (described hereinbelow) to generate variant libraries that can be expressed, screened, and assayed using the methods described herein. Mutagenesis and directed evolution methods are well known in the art. See, e.g., Ling, et al., "Approaches to DNA mutagenesis: an overview," *Anal. Biochem.*, 254(2):157-78 (1997); Dale, et al., "Oligonucleotide-directed random mutagenesis using the phosphorothioate method," *Methods Mol. Biol.*, 57:369-74 (1996); Smith, "In vitro mutagenesis," *Ann. Rev. Genet.*, 19:423-462 (1985); Botstein, et al., "Strategies and applications of in vitro mutagenesis," *Science*, 229:1193-1201 (1985); Carter, "Site-directed mutagenesis," *Biochem. J.*, 237:1-7 (1986); Kramer, et al., "Point Mismatch Repair," *Cell*, 38:879-887 (1984); Wells, et al., "Cassette mutagenesis: an efficient method for generation of multiple mutations at defined sites," *Gene*, 34:315-323 (1985); Minshull, et al., "Protein evolution by molecular breeding," *Current Opinion in Chemical Biology*, 3:284-290 (1999); Christians, et al., "Directed evolution of thymidine kinase for AZT phosphorylation using DNA family shuffling," *Nature Biotechnology*, 17:259-264 (1999); Crameri, et al., "DNA shuffling of a family of genes from diverse species accelerates directed evolution," *Nature*, 391:288-291; Crameri, et al., "Molecular evolution of an arsenate detoxification pathway by DNA shuffling," *Nature Biotechnology*, 15:436-438 (1997); Zhang, et al., "Directed evolution of an effective fucosidase from a galactosidase by DNA shuffling and screening," *Proceedings of the National Academy of Sciences, U.S.A.*, 94:45-4-4509; Crameri, et al., "Improved green fluorescent protein by molecular evolution using DNA shuffling," *Nature Biotechnology*, 14:315-319 (1996); Stemmer, "Rapid evolution of a protein in vitro by DNA shuffling," *Nature*, 370:389-391 (1994); Stemmer, "DNA shuffling by random fragmentation and reassembly: In vitro recombination for molecular evolution," *Proceedings of the National Academy of Sciences, U.S.A.*, 91:10747-10751 (1994); WO 95/22625; WO 97/0078; WO 97/35966; WO 98/27230; WO 00/42651; and WO 01/75767, all of which are incorporated herein by reference.

CBH2 Polynucleotides

The present invention provides isolated or recombinant polynucleotides that encode any of the above-described CBH2 polypeptide variants.

Those having ordinary skill in the art will readily appreciate that due to the degeneracy of the genetic code, a multitude of nucleotide sequences encoding CBH2 polypeptides of the present invention exist. Table 1 is a Codon Table that provides the synonymous codons for each amino acid. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Such "silent variations" are one species of "conservative" variation. One of ordinary skill in the art will recognize that each codon in a nucleic acid (except AUG, which is ordinarily the only codon for methionine) can be modified by standard techniques to encode a functionally identical polypeptide. Accordingly, each silent variation of a nucleic acid which encodes a polypeptide is implicit in any described sequence. The invention contemplates and provides each and every possible variation of nucleic acid sequence encoding a polypeptide of the invention that could be made by selecting combinations based on possible codon choices. These combinations are made in accordance with the standard triplet genetic code (set forth in Table 1), as applied to the polynucleotide sequences of the present invention.

A group of two or more different codons that, when translated in the same context, all encode the same amino acid, are referred to herein as "synonymous codons." CBH2 polynucleotides of the present invention may be codon optimized for expression in a particular host organism by modifying the polynucleotides to conform with the optimum codon usage of the desired host organism. Those having ordinary skill in the art will recognize that tables and other references providing preference information for a wide range of organisms are readily available See e.g., Henaut and Danchin in "*Escherichia coli* and *Salmonella*," Neidhardt, et al. Eds., ASM Pres, Washington D.C. (1996), pp. 2047-2066, which is incorporated herein by reference.

The terms "conservatively modified variations" and "conservative variations" are used interchangeably herein to refer to those nucleic acids that encode identical or essentially identical amino acid sequences, or in the situation where the nucleic acids are not coding sequences, the term refers to nucleic acids that are identical. One of ordinary skill in the art will recognize that individual substitutions, deletions or additions which alter, add or delete a single amino acid or a small percentage of amino acids in an encoded sequence are considered conservatively modified variations where the alterations result in one or more of the following: the deletion of an amino acid, addition of an amino acid, or substitution of an amino acid with a chemically similar amino acid. When more than one amino acid is affected, the percentage is typically less than 5% of amino acid residues over the length of the encoded sequence, and more typically less than 2%. References providing amino acids that are considered conservative substitutions for one another are well known in the art.

An exemplary CBH2 polynucleotide sequence of the present invention is provided as SEQ ID NO: 3, which is a polynucleotide sequence that encodes wild type *Streptomyces* sp. CBH2 (SEQ ID NO: 4), but which has been codon optimized to express well in both *Bacillus megaterium* and *Escherichia coli*, as described in Example 1, hereinbelow. Other specific changes have been identified in polynucleotides of the present invention that differ from the corresponding wild type polynucleotide sequence. The present invention further provides an isolated or recombinant cbh2 polynucleotide having a polynucleotide sequence comprising one or more substitutions selected from the group consisting of t84c; a240g; t252c; a300g; a411g; t570c; a636g; c648t; a819g; c822t; t828a; a840t; c930t; t939a; t993c; a1122g; a1147t; g1148c; c1149a; g1155a; and t1263c, wherein nucleotide position is determined by optimal alignment with SEQ ID NO: 3. Illustrative variants having these silent mutations are provided in Example 9.

Further polynucleotides encompassed by the invention include polynucleotide sequences encoding variant CBH2 polypeptides having at least 95% (e.g., 96%, 97%, 98%, 99% and even 100%) sequence identity to SEQ ID NO: 6. In some exemplary embodiments, the polynucleotide sequence will have at least 90% (e.g., 93%, 95%, 96%, 97%, 98%, 99% or even 100%) sequence identity to the polynucleotide sequence of SEQ ID NO: 5 illustrated below.

(SEQ ID NO: 5)
ATGGGGCCTGCTGCACCTACTGCACGTGTGGATAATCCTTATG

TAGGCGCGACAATGTACGTAAATCCAGAATGGTCAGCTCTTGC

TGCTTCGGAACCAGGTGGTGATCGTGTTGCAGATCAACCTACG

GCTGTTTGGTTAGATCGTATTGCAACTATTGAAGGTGTTGATG

GAAAAATGGGATTACGAGAACATCTTGATGAAGCGTTACAACA

AAAAGGAAGCGGAGAACTTGTGGTACAGTTAGTAATTTATGAT

TTACCTGGTCGTGATTGCGCGGCTCTTGCTAGTAATGGTGAAT

TAGGTCCTGATGAATTAGATCGATATAAAAGCGAATATATTGA

TCCGATTGCAGACATTTTATCGGATTCCAAATATGAAGGACTT

CGTATTGTTACGGTTATTGAACCAGACAGCTTACCTAATTTAG

TAACAAACGCAGGTGGTACAGATACAACGACAGAAGCATGTAC

TACTATGAAAGCAAACGGTAATTATGAAAAAGGGGTATCGTAT

-continued
GCGCTTTCTAAATTAGGTGCAATTCCGAACGTATACAACTATA

TTGATGCTGCTCATCATGGATGGTTAGGATGGGACACAAATTT

TGGGCCATCCGTACAGGAATTTTATAAAGTGGCAACATCAAAT

GGCGCATCCGTTGATGATGTGGCGGGATTTGCAGTCAATACAG

CTAATTATTCAGCAACTGTAGAACCTTATTTTACGGTTTCAGA

TACGGTGAATGGGCAGACGGTACGTCAATCTAAATGGGTTGAC

TGGAATCAATACGTAGATGAACAAAGTTATGCGCAGGCTTTAC

GAAACGAAGCTGTCGCCGCTGGATTTAATAGCGATATTGGTGT

GATTATTGATACATCCCGAAATGGATGGGTGGTCCAGATCGC

CCTTCAGGGCCTGGCCCTCAAACTTCCGTAGATGCTTATGTAG

ATGGATCACGAATTGATCGTCGCGTTCATGTAGGAAATTGGTG

TAATCAGTCTGGAGCAGGCTTAGGTGAAAGACCAACAGCAGCA

CCAGCTAGCGGGATTGATGCATATACATGGATTAAACCGCCGG

GCGAATCTGATGGAAATTCAGCTCCGGTTGATAATGACGAAGG

AAAAGGATTTGACCGTATGTGTGATCCTAGCTACCAGGGAAAC

GCTCGCAATGGCTACAATCCTTCAGGAGCGTTACCTGATGCAC

CATTAAGTGGACAATGGTTTTCGGCACAATTTCGTGAATTAAT

GCAAAATGCATATCCTCCATTATCTTGA

Other exemplary polynucleotides according to the invention include polynucleotides that code for a CBH2 variant having at least 90% (e.g. at least 92%, 93%, 94%, 95%, 96%, 97%, 98% and 99%) sequence identity to SEQ ID NO: 8. In some exemplary embodiments, the polynucleotide sequence will have at least 90% (e.g., 93%, 95%, 96%, 97%, 98%, 99% or even 100%) sequence identity to the polynucleotide sequence of SEQ ID NO: 7 illustrated below.

(SEQ ID NO: 7)
ATGGGGCCTGCTGCACCTACTGCACGTGTGGATAATCCTTATG

TAGGCGCGACAATGTACGTAAATCCAGAATGGTCAGCTCTTGC

TGCTTCGGAACCAGGTGGTGATCGTGTTGCAGATCAACCTACG

GCTGTTTGGTTAGATCGTATTGCAACTATTGAAGGTGTTGATG

GAAAAATGGATTACGAGAACATCTTGATGAAGCGTTACAACA

AAAAGGAAGCGGAGAACTTGTGGTACAGTTAGTAATTTATGAT

TTACCTGGTCGTGATTGCGCGGCTCTTGCTAGTAATGGTGAAT

TAGGTCCTGATGAATTAGATCGATATAAAAGCGAATATATTGA

TCCGATTCGTGACATTTTATCGGATTCCAAATATGAAGGACTT

CGTATTGTTACGGTTATTGAACCAGACAGCTTACCTAATTTAG

TAACAAACGCAGGTGGTACAGATACAACGACAGAAGCATGTAC

TACTATGAAAGCAAACGGTAATTATGAAAAAGGGGTATCGTAT

GCGCTTTCTAAATTAGGTGCAATTCCGAACGTATACAACTATA

TTGATGCTGCTCATCATGGATGGTTAGGATGGGACACAAATTT

TGGGCCATCCGTACAGGAATTTTATAAAGTGGCAACATCAAAT

GGCGCATCCGTTGATGATGTGGCGGGATTTGCAGTCAATACAG

-continued
CTAATTATTCAGCAACTGTAGAACCTTATTTTACGGTTTCAGA

TACGGTGAATGGGCAGACGGTACGTCAATCTAAATGGGTTGAC

TGGAATCAATACGTAGATGAACAAAGTTATGCGCAGGCTTTAC

GAAACGAAGCTGTCGCCGCTGGATTTAATAGCGATATTGGTGT

GATTATTGATACATCCCGAAATGGATGGGTGGTCCAGATCGC

CCTTCAGGGCCTGGCCCTCAAACTTCCGTAGATGCTTATGTAG

ATGGATCACGAATTGATCGTCGCGTTCATGTAGGAAATTGGTG

TAATCAGTCTGGAGCAGGCTTAGGTGAAAGACCAACAGCAGCA

CCAGCTAGCGGGATTGATGCATATACATGGATTAAACCGCCGG

GCGAATCTGATGGAAATTCAGCTCCGGTTGATAATGACGAAGG

AAAAGGATTTGACCGTATGTGTGATCCTAGCTACCAGGGAAAC

GCTCGCAATGGCTACAATCCTACCGGAGCGTTACCTGATGCAC

CATTAAGTGGACAATGGTTTTCGGCACAATTTCGTGAATTAAT

GCAAAATGCATATCCTCCATTATCTTGA

CBH2 polynucleotides of the present invention may further comprise a polynucleotide encoding a signal peptide as described in more detail below under the heading "Vectors, Promoters, and Expression Systems".

Polynucleotides of the present invention can be prepared using methods that are well known in the art. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al. (1981) Tetrahedron Letters, 22:1859-69, or the method described by Matthes, et al. (1984) EMBO J., 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others.

Polynucleotides may also be synthesized by well-known techniques as described in the technical literature. For example, see, Carruthers, et al., *Cold Spring Harbor Symp. Quant. Biol.*, 47:411-418 (1982) and Adams, et al., *J. Am. Chem. Soc.*, 105:661 (1983), both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel"), all of which are incorporated herein by reference. Examples of protocols sufficient to direct persons of skill through in vitro amplification methods, including the polymerase chain reaction (PCR) and the ligase chain reaction (LCR) are known and reference is made to Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564, all of which are incorporated herein by reference. Improved methods for cloning in vitro amplified nucleic acids are described in Wallace et al., U.S. Pat. No. 5,426,039, which is incorporated herein by reference.

Vectors, Promoters, and Expression Systems

The present invention also includes recombinant genetic constructs comprising one or more of the CBH2 polynucleotide sequences as broadly described above. The term "construct", "DNA construct", or "nucleic acid construct" refers herein to a nucleic acid, either single- or double-stranded, which is isolated from a naturally occurring gene or which has been modified to contain segments of nucleic acids in a manner that would not otherwise exist in nature. The term "nucleic acid construct" is synonymous with the term "expression cassette" when the nucleic acid construct contains the control sequences required for expression of a CBH2 coding sequence of the present invention.

The present invention also provides an expression vector comprising a CBH2 polynucleotide of the present invention operably linked to a promoter. Example 1 provides a description of how to make constructs for expression of CBH2. However, one skilled in the art is aware of means for making DNA constructs. The term "control sequences" refers herein to all the components that are necessary or advantageous for the expression of a polypeptide of the present invention. Each control sequence may be native or foreign to the nucleotide sequence encoding the polypeptide. Such control sequences include, but are not limited to, a leader, promoter, signal peptide sequence, and transcription terminator. At a minimum, the control sequences include a promoter and transcriptional and translational stop signals. In some embodiments, the control sequence may include a polyadenylation sequence. The control sequences may be provided with linkers for the purpose of introducing specific restriction sites facilitating ligation of the control sequences with the coding region of the nucleotide sequence encoding a polypeptide.

The term "operably linked" refers herein to a configuration in which a control sequence is appropriately placed at a position relative to the coding sequence of the DNA sequence such that the control sequence influences the expression of a polypeptide. When used herein, the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

As used herein, the term "expression" includes any step involved in the production of the polypeptide including, but not limited to, transcription, post-transcriptional modification, translation, post-translational modification, and secretion.

The term "expression vector" refers herein to a DNA molecule, linear or circular, that comprises a segment encoding a polypeptide of the invention, and which is operably linked to additional segments that provide for its transcription.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

Polynucleotides of the present invention can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

When incorporated into an expression vector, a CBH2 polynucleotide of the invention is operatively linked to an appropriate transcription control sequence (promoter) to direct mRNA synthesis, e.g., T5 promoter. Examples of such transcription control sequences particularly suited for use in transgenic plants include the cauliflower mosaic virus (CaMV) and figwort mosaic virus (FMV). Other promoters known to control expression of genes in prokaryotic or eukaryotic cells or their viruses and which can be used in some embodiments of the invention include SV40 promoter, *E. coli* lac or trp promoter, phage lambda $P_L$ promoter, tac promoter, T7 promoter, and the like. Examples of suitable promoters useful for directing the transcription of the nucleotide constructs of the present invention in a filamentous fungal host cell are promoters such as cbh1, cbh2, eg11, eg12, pepA, hfb1, hfb2, xynl, amy, and glaA (Nunberg et al., Mol. Cell. Biol., 4:2306-2315 (1984), Boel et al., *EMBO J.* 3:1581-1585 ((1984) and EPA 137280). In bacterial host cells, suitable promoters include the promoters obtained from the *E. coli* lac operon, *Streptomyces coelicolor* agarase gene (dagA), *Bacillus subtilis* levansucranse gene (sacB), *Bacillus licheniformis* alpha-amylase gene (amyl), *Bacillus stearothermophilus* maltogenic amylase gene (amyM), *Bacillus amyloliquefaciens* alpha-amylase gene (amyQ), *Bacillus subtilis* stress gene 39 (ydaD), *Bacillus subtilis* xylA and xylB genes, and the prokaryotic beta-lactamase gene. Other useful promoters include the xylose promoter xyl (Rygus and Hillen, 1991, *Appl. Microbiol. Biotechnol.* 35:594-599) and the *Bacillus megaterium* promoter Inha, which is described in U.S. Ser. No. 12/760,827, filed Apr. 15, 2010, which is incorporated herein by reference.

An expression vector optionally contains a ribosome binding site for translation initiation, and a transcription terminator, such as PinII The vector also optionally includes appropriate sequences for amplifying expression, e.g., an enhancer.

The vector or DNA construct may also generally include a signal peptide coding region that codes for an amino acid sequence linked to the amino terminus of a polypeptide and which directs the encoded polypeptide into the cells secretory pathway. Signal peptides that are suitable for use in the practice of the present invention include the *Bacillus megaterium* nprM signal peptide sequence as shown in FIG. 1B.

Other effective signal peptide coding regions for bacterial host cells may be obtained from the genes of *Bacillus* NCIB 11837 maltogenic amylase, *B. stearothermophilus* alpha-amylase, *B. licheniformis* subtilisin, *B. licheniformis* beta-lactamase, *B. stearothermophilus* neutral proteases (nprT, nprS, nprM) and *B. subtilis* prsS. The penicillin G acylase signal peptide of *Bacillus megaterium* may also be used. Further signal sequences are described in Simonen and Palva (1993), *Microbiological Reviews* 57:109-137.

Effective signal peptides coding regions for filamentous fungal host cells include but are not limited to the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase and *Humicola lanuginosa* lipase.

In addition, expression vectors of the present invention optionally contain one or more selectable marker genes to provide a phenotypic trait for selection of transformed host cells. Suitable marker genes include those coding for antibiotic resistance such as, ampicillin, kanamycin, chloramphenicol, or tetracycline resistance. Further examples include the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Additional selectable marker genes include dihydrofolate reductase or neomycin resistance for eukaryotic cell culture, and tetracycline or ampicillin resistance in *E. coli*.

An exemplary expression vector for the expression of CBH2 polypeptides of the present invention is described in Example 1, hereinbelow. Vectors of the present invention can be employed to transform an appropriate host to permit the host to express an invention protein or polypeptide.

CBH2 polynucleotides of the invention can also be fused, for example, in-frame to nucleic acids encoding a secretion/localization sequence, to target polypeptide expression to a desired cellular compartment, membrane, or organelle of a cell, or to direct polypeptide secretion to the periplasmic space or into the cell culture media. Such sequences are known to those of skill, and include secretion leader peptides, organelle targeting sequences (e.g., nuclear localization sequences, endoplasmic reticulum (ER) retention signals, mitochondrial transit sequences, peroxisomal transit sequences, and chloroplast transit sequences), membrane localization/anchor sequences (e.g., stop transfer sequences, GPI anchor sequences), and the like.

Expression Hosts

The present invention also provides engineered (recombinant) host cells that are transformed with a vector or genetic construct of the invention (e.g., an invention cloning vector or an invention expression vector), as well as the production of CBH2 polypeptide variants of the invention by a transformed host cell. Thus, the present invention is directed to a host cell comprising a polynucleotide encoding any of the CBH2 variants of the present invention described herein. As used herein, a genetically modified or recombinant host cell includes the progeny of said host cell that comprises a CBH2 polynucleotide which encodes a recombinant or variant polypeptide of the invention.

In some embodiments, the genetically modified or recombinant host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. Particularly preferred fungal host cells are yeast cells and filamentous fungal cells. The filamentous fungi host cells of the present invention include all filamentous forms of the subdivision Eumycotina and Oomycota. See, for example, Hawksworth et al., In Ainsworth and Bisby's Dictionary of The Fungi, 8$^{th}$ edition, 1995, CAB International, University Press, Cambridge, UK, which is incorporated herein by reference. Filamentous fungi are characterized by a vegetative mycelium with a cell wall composed of chitin, cellulose and other complex polysaccharides. The filamentous fungi host cells of the present invention are morphologically distinct from yeast.

In the present invention, a filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms or taxonomic equivalents thereof.

In some embodiments of the invention, the filamentous fungal host cell is of the, *Aspergillus* species, *Ceriporiopsis* species, *Chrysosporium* species, *Corynascus* species, *Fusarium* species, *Humicola* species, *Neurospora* species, *Penicillium* species, *Tolypocladium* species, *Tramates* species, or *Trichoderma* species.

In some embodiments of the invention, the filamentous fungal host cell is of the *Trichoderma* species, e.g., *T. longibrachiatum, T. viride* (e.g., ATCC 32098 and 32086), *Hypocrea jecorina* or *T. reesei* (NRRL 15709, ATTC 13631, 56764, 56765, 56466, 56767 and RL-P37 and derivatives thereof (See Sheir-Neiss et al., Appl. Microbiol. Biotechnology, (1984) pp 46-53), *T. koningii*, and *T. harzianum*). In addition, the term "*Trichoderma*" refers to any fungal strain that was previously classified as *Trichoderma* or currently classified as *Trichoderma*.

In some embodiments of the invention, the filamentous fungal host cell is of the *Aspergillus* species, e.g., *A. awamori, A. funigatus, A. japonicus, A. nidulans, A. niger, A. aculeatus, A. foetidus, A. oryzae, A. sojae, and A. kawachi*. (Reference is made to Kelly and Hynes (1985) *EMBO J.* 4,475479; NRRL 3112, ATCC 11490, 22342, 44733, and 14331; Yelton M., et al., (1984) *Proc. Natl. Acad. Sci. USA*, 81, 1470-1474; Tilburn et al., (1982) *Gene* 26, 205-221; and Johnston, I. L. et al. (1985) *EMBO J.* 4, 1307-1311, all of which are incorporated herein by reference).

In some embodiments of the invention, the filamentous fungal host cell is of the *Chrysosporium* species, e.g., *C. lucknowense, C. keratinophilum, C. tropicum, C. merdarium, C. Mops, C. pannicola*, and *C. zonatum*.

In some embodiments of the invention, the filamentous fungal host cell is of the *Fusarium* species, e.g., *F. bactridioides, F. cerealis, F. crookwellense, F. culmorum, F.*

*graminearum, F. graminum, F. oxysporum, F. roseum*, and *F. venenatum*. In some embodiments of the invention, the filamentous fungal host cell is of the *Neurospora* species, e.g., *N. crassa*. Reference is made to Case, M. E. et al., (1979) *Proc. Natl. Acad. Sci. USA*, 76, 5259-5263; U.S. Pat. No. 4,486,553; and Kinsey, J. A. and J. A. Rambosek (1984) *Molecular and Cellular Biology* 4, 117-122, all of which are incorporated herein by reference. In some embodiments of the invention, the filamentous fungal host cell is of the *Humicola* species, e.g., *H. insolens, H. grisea*, and *H. lanuginosa*. In some embodiments of the invention, the filamentous fungal host cell is of the *Mucor* species, e.g., *M. miehei* and *M. circinelloides*. In some embodiments of the invention, the filamentous fungal host cell is of the *Rhizopus* species, e.g., *R. oryzae* and *R. niveus*. In some embodiments of the invention, the filamentous fungal host cell is of the *Penicillum* species, e.g., *P. purpurogenum, P. chrysogenum*, and *P. verruculosum*. In some embodiments of the invention, the filamentous fungal host cell is of the *Thielavia* species, e.g., *T. terrestris*. In some embodiments of the invention, the filamentous fungal host cell is of the *Tolypocladium* species, e.g., *T. inflatum* and *T. geodes* or of the *Trichoderma* species, e.g., *T. reesei*. In some embodiments of the invention, the filamentous fungal host cell is of the *Trametes* species, e.g., *T. villosa* and *T. versicolor*.

In the present invention, a yeast host cell may be a cell of a species of, but not limited to *Candida, Hansenula, Saccharomyces, Schizosaccharomyces, Pichia, Kluyveromyces*, and *Yarrowia*. In some embodiments of the invention, the yeast cell is *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, and *Yarrowia lipolytica*.

In some embodiments on the invention, the host cell is an algal such as, *Chlamydomonas* (e.g., *C. Reinhardtii*) and *Phormidium* (P. sp. ATCC29409). In other embodiments, the host cell is a prokaryotic cell. Suitable prokaryotic cells include gram positive, gram negative and gram-variable bacterial cells. The host cell may be a species of, but not limited to *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas*.

In some embodiments, the host cell is a species of *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces*, and *Zymomonas*.

In yet other embodiments, the bacterial host strain is non-pathogenic to humans. In some embodiments the bacterial host strain is an industrial strain. Numerous bacterial industrial strains are known and suitable in the present invention.

In some embodiments of the invention, the bacterial host cell is of the *Agrobacterium* species, e.g., *A. radiobacter, A. rhizogenes*, and *A. rubi*. In some embodiments of the invention, the bacterial host cell is of the *Arthrobacter* species, e.g., *A. aurescens, A. citreus, A. globformis, A. hydrocarboglutamicus, A. mysorens, A. nicotianae, A. paraffineus, A. protophonniae, A. roseoparqffinus, A. sulfureus*, and *A. ureafaciens*. In some embodiments of the invention, the bacterial host cell is of the *Bacillus* species, e.g., *B. thuringiensis, B. anthracia, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. Some preferred embodiments of a *Bacillus* host cell include *B. subtilis, B. licheniformis, B. megaterium, B. stearothermophilus* and *B. amyloliquefaciens*. In some embodiments, the bacterial host cell is of the *Clostridium* species, e.g., *C. acetobutylicum, C. tetani* E88, *C. lituseburense, C. saccharobutylicum, C. perfringens*, and *C. beijerinckii*. In some embodiments the bacterial host cell is of the *Corynebacterium* species e.g., *C. glutamicum* and *C. acetoacidophilum*. In some embodiments, the bacterial host cell is of the *Escherichia* species, e.g., *E. coli*. In some embodiments, the bacterial host cell is of the *Erwinia* species, e.g., *E. uredovora, E. carotovora, E. ananas, E. herbicola, E. punctata*, and *E. terreus*. In some embodiments, the bacterial host cell is of the *Pantoea* species, e.g., *P. citrea*, and *P. agglomerans*. In some embodiments, the bacterial host cell is of the *Pseudomonas* species, e.g., *P. putida, P. aeruginosa, P. mevalonii*, and *P.* sp. D-01 10. In some embodiments, the bacterial host cell is of the *Streptococcus* species, e.g., *S. equisimiles, S. pyogenes*, and *S. uberis*. In some embodiments, the bacterial host cell is of the *Streptomyces* species, e.g., *S. ambofaciens, S. achromogenes, S. avermitilis, S. coelicolor, S. aureofaciens, S. aureus, S. fungicidicus, S. griseus*, and *S. lividans*. In some embodiments, the bacterial host cell is of the *Zymomonas* species, e.g., *Z. mobilis*, and *Z. lipotyfica*.

Strains that may be used in the practice of the invention including both prokaryotic and eukaryotic strains are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Introduction of a vector or DNA construct into a host cell can be effected by calcium phosphate transfection, DEAE-Dextran mediated transfection, electroporation, or other common techniques (See Davis, L., Dibner, M. and Battey, I. (1986) *Basic Methods in Molecular Biology*, which is incorporated herein by reference). In one embodiment, the vector or DNA construct is stably integrated into the chromosome of a desired host cell. In some embodiments, the procedure for integration includes the construction of a vector that has a temperature sensitive origin of replication and around 1 kb of target sequence (for example nprM loci) immediately upstream of a promoter—CBH2, to target integration to the nprM locus. The vector may be subsequently transformed into the desired host (for example a *B. megaterium* strain). Integration may be achieved by growing the transformants overnight in appropriate selection media at high temperature (42° C.) and then integrants confirmed by PCR.

The engineered host cells can be cultured in conventional nutrient media modified as appropriate for activating promoters, selecting transformants, or amplifying the polynucleotide encoding the CBH2 variant. Culture conditions, such as temperature, pH and the like, are those previously used with the host cell selected for expression, and will be apparent to those skilled in the art and in the references cited herein, including, for example, Sambrook, Ausubel and Berger, as well as, for example, Freshney (1994) *Culture of Animal Cells, a Manual of Basic Technique*, third edition, Wiley-Liss, New York; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla., all of which are incorporated herein by reference.

Production and Recovery of β-Glucosidase Polypeptide Variants

The present invention is directed to a method of producing a CBH2 polypeptide variant having cellulase activity, the method comprising providing a host cell transformed with a polynucleotide encoding a CBH2 polypeptide variant of the present invention; culturing the transformed host cell in a culture medium under conditions that cause said polynucleotide to express the encoded variant; and optionally recovering or isolating the expressed CBH2 polypeptide variant, or recovering or isolating the culture medium containing the expressed CBH2 polypeptide variant. The method further provides optionally lysing the transformed host cells after expressing the CBH2 polypeptide variant and optionally recovering or isolating the expressed variant from the cell lysate. In some embodiments, the invention is directed to the culture media which comprises the CBH2 polypeptide variant produced by the method described above. In some embodiments, the transformed host cell may produce additional cellulase polypeptides. The additional cellulase polypeptides may be from the expression of polynucleotides encoding endogenous cellulases or from the expression of polynucleotides encoding heterologous cellulase polypeptides.

Typically, recovery or isolation of the polypeptide variant is from the host cell culture medium, the host cell or both, using protein recovery techniques that are well known in the art, including those described herein.

In some embodiments, following transformation of a suitable host strain and growth (cultivating or culturing) of the host strain to an appropriate cell density, a selected promoter may be induced by appropriate means (e.g., temperature shift or chemical induction) and cells are cultured for an additional period. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelli, et al., (1989) *In vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference.

In some embodiments, cells expressing the CBH2 polypeptide variants of the invention are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady sate growth conditions. Methods for modulating nutrients and growth factors for continuous fermentation processes as well as techniques for maximizing the rate of product formation are well known in the art of industrial microbiology.

The resulting variant polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic, chromatofocusing, and size exclusion), or precipitation. Protein refolding steps can be used, as desired, in completing the configuration of the mature protein. Finally, high performance liquid chromatography (HPLC) can be employed in the final purification steps. In addition to the references noted supra, a variety of purification methods are well known in the art, including, for example, those set forth in Sandana (1997) *Bioseparation of Proteins*, Academic Press, Inc.; Bollag et al. (1996) *Protein Methods*, 2nd Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* 3rd *Edition,* Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, all of which are incorporated herein by reference. Exemplary procedures for producing CBH2 variants are provided in Examples 2 through 5, hereinbelow. The skilled artisan will readily appreciate that this procedure can be used to produce the CBH2 polypeptide variants of the present invention.

Cell-free transcription/translation systems can also be employed to produce CBH2 polypeptides using the polynucleotides of the present invention. Several such systems are commercially available. A general guide to in vitro transcription and translation protocols is found in Tymms (1995) *In vitro Transcription and Translation Protocols: Methods in Molecular Biology*, Volume 37, Garland Publishing, NY, which is incorporated herein by reference.

Methods of Using CBH2 Polypeptides and Related Compositions

As described supra, CBH2 polypeptide variants of the present invention can be used to catalyze the hydrolysis of cellulose substrates with the release of oligosaccharide groups containing from 2 to 3 glucose units. Thus, the present invention provides a method for producing cellobiose, said method comprising: (a) providing a feedstock comprising cellulosic biomass and (b) contacting the feedstock with a effective amount of a CBH2 polypeptide variant of the invention under conditions sufficient to form a reaction mixture for converting the feedstock to cellobiose. The CBH2 polypeptide variant may be utilized in such methods in either isolated form or as part of a composition, such as any of those described herein (e.g. in a culture media comprising the CBH2 polypeptide variant produced by a cultured transformed host cell). The method may further comprise producing glucose from the produced cellobiose comprising contacting the cellobiose with an effective amount of β-glucosidase under conditions sufficient to form a reaction mixture for converting the cellobiose to glucose.

In some embodiments, the CBH2 is combined with other cellulases to form a cellulase mixture. The cellulase mixture may include cellulases selected from CBH, EG and BG cellulases (e.g., cellulases from *Trichoderma reesei* (e.g., C2730 Cellulase from *Trichoderma reesei* ATCC No. 25921, Sigma-Aldrich, Inc.), C9870 ACCELLERASE™ 1500, Genencor, Inc., and the like), *Acidothennus cellulolyticus, Thermobifida fusca, Humicola grisea, Myceliophthora* sp., and *Chrysosporium* sp.). The enzymes of the cellulase mixture work together resulting in decrystallization and hydrolysis of cellulose from a biomass substrate to yield soluble sugars such as but not limited to glucose (See Brigham et al., (1995) in Handbook on Bioethanol (C. Wyman ed.) pp 119-141, Taylor and Francis, Washington D.C., which is incorporated herein by reference). CBH2 polypeptide variants of the present invention may be used in combination with other optional ingredients such as a buffer, a surfactant, and/or a scouring agent.

CBH2 polypeptide variants of the present invention, as well as any composition, culture medium, or cell lysate comprising such variants, may be used in the production of monosaccharides, disaccharides, or oligomers of a mono- or di-saccharide as chemical or fermentation feedstock from biomass. As used herein, the term "biomass" refers to living or dead biological material that contains a polysaccharide substrate, such as, for example, cellulose, starch, and the like. Therefore, the present invention provides a method of converting a biomass substrate to a fermentable sugar, the method comprising contacting a CBH2 polypeptide variant encompassed by the invention or an enzyme composition comprising a CBH2 polypeptide variant according to the invention with the biomass substrate under conditions suitable for the production of the fermentable sugar. The enzyme composition may be derived from a culture medium (whole broth) or cell lysate comprising the CBH2 polypeptide variant or the enzyme composition may be a clarified or a purified enzyme composition. The present invention further provides a method of converting a biomass substrate to a fermentable sugar, the method comprising: (a) pretreating a cellulose containing substrate to increase its susceptibility to hydrolysis; (b) contacting the pretreated substrate of step (a) with a composition, culture medium or cell lysate containing a CBH2 polypeptide variant of the present invention under conditions suitable for the production of the fermentable sugar.

In some embodiments, the biomass includes cellulosic substrates including but not limited to, wood, wood pulp, paper pulp, corn stover, corn fiber, rice, paper and pulp processing waste, woody or herbaceous plants, fruit or vegetable pulp, distiller's grain, grasses, rice hulls, wheat straw, cotton, hemp, flax, sisal, corn cobs, sugar cane bagasse, switch grass and mixtures thereof.

Any pretreatment process known in the art may be used to disrupt the cellulose structure of the biomass substrate. Conventional pretreatment methods include, but are not limited to steam pretreatment (with or without explosion), dilute acid pretreatment, wet oxidation pretreatment hot water pretreatment, ammonia fiber pretreatment (e.g., AFEX); mechanical and physical pretreatment as well as biological pretreatment. Pretreatment is preferably carried out prior to hydrolysis with the cellulase enzymes. Non-limiting examples of these chemical pretreatment methods may be found for example in USP Application No. 20020164730 and Sassner et al., 2006, *Enzyme Microb. Technol.* 39:756-762 for steam pretreatment; Duff and Murray, 1996, *Bioresource Technol.* 855:1-33 for dilute acid pretreatment; and Gollapalli et al., 2002, *Appl. Biochem. Biotechnol.* 98:23-35 and Teymouri et al., 2005, *Bioresource Technol.* 96:2014-2018 for AFEX. Mechanical and physical pretreatments include but are not limited to various types of milling such as but not limited to wet milling or dry milling. In addition, combinations of pretreatment may be used.

In some embodiments, the CBH2 polypeptide variants compositions may be reacted with a feedstock of the biomass or pretreated biomass at a temperature in the range of about 25° C. to about 100° C., about 30° C. to about 90° C., about 30° C. to about 80° C., about 40° C. to about 80° C. and about 35° C. to about 75° C. Also the CBH2 polypeptide variants compositions may be reacted with a feedstock of the biomass or pretreated biomass at a temperature about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. In addition to the temperatures described above, conditions suitable for converting a biomass substrate to a fermentable sugar that employs a CBH2 polypeptide variant of the present invention include carrying out the process at a pH in a range from about pH 3.0 to about 8.5, about pH 3.5 to about 8.5, about pH 4.0 to about 7.5, about pH 4.0 to about 7.0, about pH 4.0 to about 6.5 and about pH 4.0 to 5.5. Those having ordinary skill in the art will appreciate that the reaction times for converting a particular biomass substrate to a fermentable sugar may vary but the optimal reaction time can be readily determined. Exemplary reaction times may be in the range of from about 1.0 to about 240 hours, from about 5.0 to about 180 hrs and from about 10.0 to about 150 hrs. For example, the incubation time may be at least 1 hr, at least 5 hrs, at least 10 hrs, at least 15 hrs, at least 25 hrs, at least 50 hr, at least 100 hrs, at least 180 and the like.

Reaction of the CBH2 with the biomass substrate or pretreated biomass substrate under these conditions may result in the release of substantial amounts of the soluble sugars from the substrate. For example at least 20%, at least 30%, at least 40%, at least 50%, at least 60%, at least 70%, at least 80%, at least 90% or more soluble sugar may be available as compared to the release of soluble sugar by the native Ssp CBH2 (SEQ ID NO: 4). In some embodiments, the soluble sugars will comprise glucose, xylose, cellobiose, cellotriose, cellotetrose, cellopentose or mixtures thereof.

The fermentable and soluble sugars produced by the methods of the present invention may be used to produce an alcohol (such as, for example, ethanol, butanol, and the like). The present invention therefore provides a method of producing an alcohol, where the method comprises (a) providing a fermentable sugar, such as one produced using a CBH2 polypeptide variant of the present invention in the methods described supra; (b) contacting the fermentable sugar with a fermenting microorganism to produce the alcohol; and (c) recovering the alcohol.

In some embodiments, the composition comprising the CBH2 polypeptide variant of the present invention may be used to catalyze the hydrolysis of a biomass substrate to a fermentable sugar in the presence of a fermenting microorganism such as a yeast (e.g., *Saccharomyces* sp., such as, for example, *S. cerevisiae*, *Pichia* sp., and the like) or other C5 or C6 fermenting microorganisms that are known in the art, to produce an end-product such as ethanol. In this simultaneous saccharification and fermentation (SSF) process the fermentable sugars (e.g., glucose and/or xylose) are removed from the system by the fermentation process.

In addition, the CBH2 variants according to the invention may be used in combination with other cellulases for effective hydrolysis of biomass substrates to soluble sugars. The other cellulases may be obtained from fungal or bacterial sources or may be engineered variants thereof. The mixture of cellulases may include for example other CBH's (e.g. CBH1 and CHB2), endoglucanases (e.g., EGs) and β-glucosidases. Biomass substrates are not just composed of cellulose. Conversion of hemicellulose may also be very important and therefore an enzyme composition comprising the CBH2 variants according to the invention may also include hemicellulases, xylanases, pectinases (polygalacturonases), and lignin degrading enzymes (e.g., lignin peroxidases and oxidoreductases, such as laccases). Commercially available cellulase preparations containing various classes of cellulase include Accellerase™ (Genencor, A Danisco Division) and Celluclast® (Novozymes). In addition, CBH2 variants according to the invention may be combined with combinations of one or more enzymes such as wild type, engineered or modified glucoamylases, amylases, arabinases, carboxypeptidases, catalases, cutinases, phytases, laccases, mannanases, oxidases, proteases, xylanases and/or other cellulases. Suitable examples of useful enzymes of these different classes are known in the art. These enzyme compositions may be used for various industrial applications including alcohol production from starch containing substrates such as grains (e.g. corn, wheat and the like).

The fermentable or soluble sugars produced by the use of a composition comprising a CBH2 variant polypeptide of the present invention may also be used in the production of other end-products. such as, for example, acetone, an amino acid (e.g., glycine, lysine, and the like), an organic acid (e.g., lactic acid, and the like), glycerol, hydrocarbons, a diol (e.g., 1, 3 propanediol, butanediol, and the like) and animal feeds.

CBH2 polypeptide variants and compositions thereof may also be used in the food and beverage industry for example in the process of wine making for the efficient release of monoterpenols (see, for example, Yanai and Sato (1999) *Am. J. Enol. Eitic.*, 50:231-235, which is incorporated herein by reference) and for the preparation of glycon isoflavone-enriched tofu (see, for example, Mase et al., (2004) *J. Appl. Glycosci.*, 51:211-216, which is incorporated herein by reference). CBH2 polypeptide variants of the present invention may also be employed in detergent compositions for improved cleaning performance (see, for example, U.S. Pat. No. 7,244,605; U.S. Pat. No. 5,648,263 and WO 2004/048592, which are incorporated herein by reference). The enzymes and optionally other additives (e.g. surfactants, polymers and/or complexing agents) may be formulated as granules (e.g. non-dusting granules), liquids or slurries.

The foregoing and other aspects of the invention may be better understood in connection with the following non-limiting examples.

EXAMPLES

Example 1

Wild Type *Streptomyces* Species CBH2 (Ssp CBH2) Gene Acquisition and Construction of Expression Vectors A gene coding for *Streptomyces* species CBH2 (Ssp CBH2) was codon optimized (SEQ ID NO: 1) for expression in *B. megaterium* and *Escherichia coli* based on the reported amino acid sequence (Cloning and Sequencing of an Exoglucanase Gene from *Streptomyces* sp. M23, and Its Expression in *Streptomyces lividans* TK-24; *J. Bioscience and Bioengineering*, Vol. 99,434-436, 2005) and a codon optimization algorithm incorporated as described in Example 1 of PCT application publication WO2008042876 incorporated herein by reference. The gene was synthesized by GenScript Corporation (GenScript Corporation, 120 Centennial Ave., Piscataway, N.J. 08854, USA) and the DNA sequence verified. The gene was cloned behind a *Bacillus megaterium* signal peptide plus a spacer region (12 nucleic acids) into an *E. coli/B. megaterium* shuttle vector pSSBm24 using the BsrGI/NgoMIV cloning sites. The vector pSSBm24 is a modified vector based on the shuttle vector pMM1525 (Boca Scientific Inc., Boca Raton, Fla.). The signal peptide and gene are under the control of xylose promoter (Pxy1) regulated by the xylose repressor gene (xylR) present on the shuttle vector. The vector contained the 'rep U' origin of replication for *Bacillus* and a tetracycline resistance marker. The vector also contained the pBR322 origin of replication and an ampicillin resistance marker for maintenance in *E. coli*. The resulting plasmid (pSSBm24-Ssp CBH2) was transformed by a standard PEG-mediated method of DNA transfer into *B. megaterium* protoplasts. The Ssp CBH2 sequence from the transformants was verified (SEQ ID NO: 1). The polynucleotide sequence encoding the CBH2 that was cloned into the shuttle pSSBm24 vector is illustrated by SEQ ID NO: 3.

Example 2

Shake Flask Procedure

A single microbial colony of *Bacillus megaterium* containing a plasmid with the Ssp CBH2 gene was inoculated into 1 ml Luria-Bertani (LB) Broth (0.01 g/L Peptone from casein, 0.005 g/L yeast extract, 0.01 g/L sodium chloride) containing 10 μg/mL tetracycline. Cells were grown overnight (at least 16 hrs) in an incubator at 37° C. with shaking at 250 rpm. The culture was then diluted into 50 mL A5 media (2 g/L $(NH_4)_2SO_4$, 3.5 g/L $KH_2PO_4$, 7.3 g/L $Na_2HPO_4$, 1 g/L yeast extract, pH to 6.8), 50 μL of trace elements solution (49 g/L $MnCl_2.4H_2O$, 45 g/L $CaCl_2$, 2.5 g/L $(NH_4)Mo_{70}.O_{24}.H_2O$, 2.5 g/L $CoCl_2.6H_2O$), 750 μL of 20% glucose, 1.25 mL of 20% xylose, 75 μL of 1M $MgSO_4$, 50 μL of 10 mg/mL tetracycline, 50 μL of 2.5 g/L $FeSO_4.7H_2O$ in a 250 ml flask to an optical density at 600 nm (OD600) of 0.2 and allowed to grow at 37° C. for 16 hrs. Cells were pelleted by centrifugation (4000 rpm, 15 min, 4° C.). The clear media supernatant containing the secreted Ssp CBH2 enzyme was collected and stored at 4° C. Expression and secretion of Ssp CBH2 was confirmed by Coomassie stained SDS-PAGE.

Example 3

Microreactor Expression Procedure

A single microbial colony of *B. megaterium* containing a plasmid coding for Ssp CBH2 was inoculated into 3 ml Luria-Bertani (LB) Broth (0.01 g/L Peptone from casein, 0.005 g/L yeast extract, 0.01 g/L sodium chloride) containing 10 μg/mL tetracycline and 1% glucose. Cells were grown overnight (at least 16 hrs) in an incubator at 37° C. with shaking at 250 rpm. The culture was then diluted into 5 mL A5 broth (2.0 g/L ammonium sulfate, 7.26 g/L of disodium monohydrogen phosphate, 3.52 g/L of potassium dihydrogen phosphate, 1.0 g/L of Tastone-154 yeast extract, 1.5 mM magnesium sulfate solution, 2.5 mg/L iron sulfate septahydrate solution, and trace element solution (final concentration at 45.0 mg/L of calcium chloride, 49.0 mg/L manganese chloride tetrahydrate, 2.5 mg/L cobalt chloride hexahydrate, and 2.5 mg/L ammonium molybdate hydrate) containing 10 μg/ml tetracycline and 0.5% glucose to an optical density at 600 nm (OD600) of 0.2 and allowed to grow at 37° C. for 16 hrs in a CELLERATOR™ microreactor (MicroReactor Technologies, Inc., Mountain View, Calif.). Cells were pelleted by centrifugation (4000 rpm, 15 min, 4° C.). The clear media supernatant containing the secreted Ssp CBH2 enzyme was collected and stored at 4° C. Expression and secretion of Ssp CBH2 was confirmed by Coomassie stained SDS-PAGE.

Example 4

Inoculation Shake Flask Procedure

A single microbial colony of *B. megaterium* containing a plasmid coding for Ssp CBH2 was inoculated into 250 ml A5 broth (2.0 g/L ammonium sulfate, 7.26 g/L of disodium monohydrogen phosphate, 3.52 g/L of potassium dihydrogen phosphate, 1.0 g/L of Tastone-154 yeast extract, 1.5 ml/L of 1M magnesium sulfate solution, 1.0 ml of 2.5 g/L iron sulfate septahydrate solution, and 1.0 ml/L of trace element solution containing 45.0 g/L of calcium chloride, 49.0 g/L manganese chloride tetrahydrate, 2.5 g/L cobalt chloride hexahydrate, and 2.5 g/L ammonium molybdate hydrate) containing 10 μg/ml tetracycline and 0.5% glucose. Cells were grown overnight (at least 12 hrs) in an incubator at 30° C. with shaking at 250 rpm. When the OD600 of the culture was 3.0 to 5.0 the cells were removed from the incubator and used immediately for inoculating fermentor or alternatively stored at 4° C. for later use.

Example 5

Reference CBH2 Expression; Fermentation Procedure

In an aerated agitated 15 L fermentor, 6.0 L of growth medium containing 0.88 g/L ammonium sulfate, 1.0 g/L of sodium citrate, 12.5 g/L of dipotassium monohydrogen phosphate trihydrate, 6.25 g/L of potassium dihydrogen phosphate, 3.3 g/L of Tastone-154 yeast extract, 2.0 g/L of Phytone peptone, and 1.0 ml/L of trace element solution containing 45.0 g/L of calcium chloride, 49.0 g/L manganese chloride tetrahydrate, 2.5 g/L cobalt chloride hexahydrate, and 2.5 g/L ammonium molybdate hydrate was sterilized and brought to a temperature of 37° C. 120.0 mL of a feed solution containing 500 g/L glucose monohydrate, 12 g/L ammonium chloride and 5.0 g/L magnesium sulfate anhydrous was added. 0.083 g/L ferric ammonium citrate and 10 μg/mL tetracycline were added. The fermentor was inoculated with a late exponential culture of *B. megaterium*, containing a plasmid coding for Ssp CBH2, grown in a shake flask as described in example 3 to a starting OD600 of 3.0 to 5.0. The fermentor was agitated at 500-1200 rpm and air was supplied to the fermentation vessel at 0.6-25.0 L/min to maintain dissolved oxygen level of 50% saturation. The pH of the culture was controlled at 7.0 by addition of 28% v/v ammonium hydroxide. Growth of the culture was maintained by the addition of a feed solution containing 500 g/L glucose monohydrate, 12 g/L ammonium chloride and 5.0 g/L magnesium sulfate anhydrous. After the culture reached an OD600 of 70±10, the expression of Ssp CBH2 was induced by the addition of xylose to obtain and maintain a concentration of 0.5%. The culture was grown for another 12 hours. The culture was then chilled to 4° C. and maintained at 4° C. until harvested. Media supernatant was harvested by centrifugation at 5000G for 30 minutes in a Sorval RC12BP centrifuge at 4° C.

The clear supernatant was decanted and concentrated tenfold using a polyethersulfone polymer ultrafiltration membrane with a molecular weight cut off of 10 kDa. The concentrate was diafiltered using at least 3 volumes of 100 mM sodium acetate buffer pH 5.0. The final concentrate was dispensed into shallow containers and stored at −80° C.

Example 6

Analytical Method to Determine CBH2 Activity

CBH2 activity was determined via cellulose assay, which used Avicel (microcrystalline cellulase, from Sigma) as a substrate. In a total volume of 150 μL, 60 μL clear media supernatant containing a CBH2 enzyme was added to 200 g/L Avicel in 100-250 mM sodium acetate buffer (pH 3-6). The reaction was incubated at 50-70° C. for 24 hours. Biotransformations were quenched with 50% acetonitrile. Each plate was centrifuged, and the supernatant (150 μl) was collected and filtered through a 0.45 μm filter. Conversion of Avicel to soluble sugar oligomers was measured using an Agilent HPLC 1200 equipped with HPX-87H Ion exclusion column (300 mm×7.8 mm) with 5 mM $H_2SO_4$ at a flow rate of 0.6 ml/min at 65° C. The retention times of the cellobiose and glucose were 7.5 and 9.1 minute respectively. Detectable Ssp CBH2 activity (~20% as compared to under optimal conditions (pH 5, 50° C.)) was observed under high throughput screening conditions (pH 4, 70° C.).

Example 7

Evaluation of Ssp CBH2 Activity

The time-course activity profiles of native Ssp CBH2 and variants thereof were investigated at different temperatures and pH conditions using Avicel (200 g/L) as a substrate. The biotransformations and analytical procedures are described in Example 6. The biotransformations were conducted for 0.5, 1, 2, 6, 24, 48 and 96 hrs at (a) pH 4.0, 60° C. and (b) pH 5.0, 65° C. Samples were withdrawn and quenched for HPLC analysis. CBH2 variants exhibited higher activity than the native CBH2 and were stable up to 96 hrs at pH 4.0, 60° C. and pH 5.0, 65° C. as shown in FIG. 3A-B.

Example 8

High Throughput Process to Identify CBH2 Polypeptide Variants

Plasmid libraries containing cbh2 variant genes were transformed into *B. megaterium* and plated on Luria-Bertani (LB) agar plates containing 3 μg/mL tetracycline with a DM3 regeneration media overlay (400 mM sodium succinate dibasic, pH 7.3, 0.5% casamino acids, 0.5% yeast extract, 0.4% $K_2HPO_4$, 0.2% $KH_2PO_4$, 20 mM $MgCl_2$, 0.5% glucose and 0.2% BSA). After incubation for at least 18 hours at 30° C., colonies were picked using a Q-bot® robotic colony picker (Genetix USA, Inc., Beaverton, Oreg.) into shallow, 96-well well microtiter plates containing 180 μL LB and 10 μg/mL tetracycline. Cells were grown overnight at 37° C. with shaking at 200 rpm and 85% humidity. 20 μL of this culture was then transferred into 96-well microtiter plates (deep well) containing 380 μL A5-glucose medium and 10 μg/mL tetracycline as described in example 2. After incubation of deep-well plates at 37° C. with shaking at 250 rpm for 2 hours (OD600 0.6-0.8), recombinant gene expression by the cell cultures was induced by isopropyl thiogalactoside (IPTG) to a final concentration of 1 mM. The plates were then incubated at 37° C. with shaking at 250 rpm and 85% humidity~15-18 hours. The plates were harvested and the clear media supernatant containing the secreted CBH2 polypeptide variant was separated from cell mass by centrifugation at 4° C., 4000 rpm for 15 minutes.

The CBH2 libraries were screened in high throughput using a tiered process. CBH2 variants were screened first by high throughput derivitized sugars HPLC assay (Substrate: Avicel; pH: 4.0-5.0; temperature: 60-70° C.; time: 24 hrs). Active CBH2 variants were subsequently regrown in replicates and subjected to a second high throughput derivitized sugars HPLC assay (Substrate: Avicel; pH: 3.0-6.0; temperature: 55-70° C.; time: 24 hrs) for the identification of improved variants.

The initial step in the high throughput derivitized sugars HPLC assay was the cellulose assay to convert Avicel to soluble sugar oligomers (biotransformation). In a total volume of 150 uL, 30-60 μL of cleared supernatant containing CBH2 was added to a pyramid-bottom 96-well microtiter plate containing 90-120 μL 200 mM sodium acetate buffer, 30 mg Avicel powder and one glass bead per well, for a final Avicel concentration of 200 g/L and pH 3.0-5.0. After all additions, the reaction plate was seal with aluminum/polypropylene laminate heat seal (Velocity 11 (Menlo Park, Calif.), Cat#06643-001), and reacted at 60-70° C., with shaking for 24 hrs.

The second step of the derivatized sugars HPLC assay was accomplished in high throughput by appending an ethyl 4-aminobenzoate chromophore to the saccharide in the presence of sodium cyanoborohydride to enable direct detection of the derivatized sugars by HPLC equipped with a UV detector (derivitization). The biotransformed reaction was collected by were centrifuging the plates at 4° C., 4000 rpm, for 10 minutes. The plates were then desealed and an internal standard of 150 μL 1 mg/mL erythrose was added to each well, followed by 165 μL of acetonitrile to quench the reaction. The quenched plates were re-sealed, shaken, and then centrifuged at 4000 rpm for 5 minutes. An aliquot of 100 μL of derivatization agent (151 mM ethyl 4-aminobenzoate, 159 mM sodium cyanoborohydride in a 9 parts methanol:1 part glacial acetic acid solution) was transferred to shallow, round-bottom 96-well microtiter plates containing 100 μL of quenched supernatant. After all additions, the plate was sealed with aluminum/polypropylene laminate (Velocity 11 (Menlo Park, Calif.), Cat#06643-001) heat seal tape, and reacted at 55° C. for 16-24 hrs.

Derivatized samples were then assayed by an Agilent 1100 series HPLC using a 100×3.0 mm Onyx C18 monolith column (Phenomenex (Torrance, Calif.), Cat#CHO-8158), 3 mL/min flow rate, and 50° C. column heating. A gradient method using 20 mM ammonium formate pH 4 as mobile phase A and 98.9% acetonitrile/1% methanol/0.1% formic acid as mobile phase B was used. Derivatized cellotriose, cellobiose, glucose, xylose and erythrose had retention times of 0.67, 0.82, 1.00, 1.17, and 1.37 minutes, respectively.

Example 9

Improved Cellobiohydrolase Activities of CBH2 Polypeptide Variants

Improved CBH2 polyeptide variants were identified from the high throughput screening of various Ssp CBH2 variant libraries as described in Example 8. Table 2 depicts improvement in activities of CBH2 variants encompassed by the invention.

TABLE 2

Improved CBH2 variants derived from the native Ssp CBH2 (SEQ ID NO: 4). The variants were directly compared to CBH2 (SEQ ID NO: 4) expressed from codon optimized spp CBH2 (SEQ ID NO: 3) in screening.

| Sample No. | Amino Acid Substitutions[1] | Silent Mutations[2] | Fold improvement[3] over native CBH2 (SEQ ID NO: 4) |
|---|---|---|---|
| 1 | T52K | | + |
| 2 | D151E | | + |

TABLE 2-continued

Improved CBH2 variants derived from the native Ssp CBH2 (SEQ ID NO: 4). The variants were directly compared to CBH2 (SEQ ID NO: 4) expressed from codon optimized spp CBH2 (SEQ ID NO: 3) in screening.

| Sample No. | Amino Acid Substitutions[1] | Silent Mutations[2] | Fold improvement[3] over native CBH2 (SEQ ID NO: 4) |
|---|---|---|---|
| 3 | E64G + S218V | | + |
| 4 | L201R | | + |
| 5 | L201F | | ++ |
| 6 | E64A | | + |
| 7 | P234S | | + |
| 8 | D151T | | + |
| 9 | T153V | | + |
| 10 | T52Y | | + |
| 11 | P234A | | + |
| 12 | L201M | | + |
| 13 | T241R | | + |
| 14 | T18V | | + |
| 15 | M160Q | a636g | + |
| 16 | T159R | | + |
| 17 | D104A | | + |
| 18 | L28E + S310D + D312N + A313T + S383T + Q385T | | + |
| 19 | S383T | g1155a | + |
| 20 | E155P + T158A | | + |
| 21 | S31L | t84c | + |
| 22 | L28E + S31L | | + |
| 23 | S124P + G128D + A276L | c822t | + |
| 24 | A276L + S383T | c822t; g1155a | + |
| 25 | A276L | c822t | + |
| 26 | E77P + P234A + S299P + Q378R | | + |
| 27 | E64K + P234A + Q378R | | ++ |
| 28 | P234A + S299P + Q378R | | ++ |
| 29 | S299P + Q378R | | + |
| 30 | P234A + Q378R | | ++ |
| 31 | E64K + E77P + P234A + S299P + Q378R | | ++ |
| 32 | E77P + P234A + Q378R | | ++ |
| 33 | E64K + P234A + S299P + Q378R | | ++ |
| 34 | E77P + P234A + V287F + S299P + Q378R | | ++ |
| 35 | V287F + S299P + V311L | | + |
| 36 | P234A + V287F + V311L | | ++ |
| 37 | E77P + P234A + S299P + V311L + Q378R | | + |
| 38 | E77P + P234A + S299P + G304R | | ++ |
| 39 | E77P + P234A | | ++ |
| 40 | P357T + Q378R | | + |
| 41 | P234A + A271L | | ++ |
| 42 | A51T + T159R + L201F + P234A + D312N + S383T | c930t; t939a; t993c; g1155a | ++++ |
| 43 | M19G + T159R + L201R + S383T | g1155a | +++ |
| 44 | M19G + T159R + L201F + D312N + Q385T | c930t; t939a; a1147t; g1148c; c1149a | ++ |
| 45 | M19G + L201F + N274P + D312N + Q385T | c648t; t828a; t939a; a1147t; g1148; c1149a | + |
| 46 | M19G + S31L + L201F + P234S + Q261R + D312N + S383T | t84c; a411g; c930t; t939a; g1155a | ++ |
| 47 | V183G + L201F | | ++ |
| 48 | S31L + T159R + L201F + S299P + S303T + A313T | t84c | ++ |
| 49 | S31L + T159R + L201R + P234A + T245M + S383T + Q385T | t84c | ++ |
| 50 | T159R + L201F + P234S + S383T + Q385T | a840t | ++++ |
| 51 | K110R + L201F + Q385T | a1147t; g1148c; c1149a | +++ |
| 52 | T159R + L201F + P234S + K255R + Q385T | a1147t; g1148c; c1149a | ++++ |
| 53 | A226T + P234S + V368D | | + |
| 54 | T159R + L201R + D312N + Q385T | t252c; t570c; c930t; t939a a1147t; g1148c; c1149a | + |
| 55 | M19G + S31L + T159R + L201F + P234S + D312N | t84c; c930t; t939a | ++++ |

TABLE 2-continued

Improved CBH2 variants derived from the native Ssp CBH2 (SEQ ID NO: 4). The variants were directly compared to CBH2 (SEQ ID NO: 4) expressed from codon optimized spp CBH2 (SEQ ID NO: 3) in screening.

| Sample No. | Amino Acid Substitutions[1] | Silent Mutations[2] | Fold improvement[3] over native CBH2 (SEQ ID NO: 4) |
|---|---|---|---|
| 56 | T159R + L201R + S383T | a819g; g1155a | + |
| 57 | S31L + V183I + L201F + P234S + Q385T | a240g; a1147t; g1148c; c1149a | ++++ |
| 58 | E68G + L201F + P234A + D312N + S383T + Q385T | t84c; c930t; t939a; a1122g | ++++ |
| 59 | T159R + L201F + S383T + Q385T | a729g; t828a | +++ |
| 60 | L201F + P234A + S383T | g1155a | + |
| 61 | M19G + L201F + P234S + S383T + Q385T | | + |
| 62 | L201F + P234A | t84c | + |
| 63 | M19G + T159R + L201F + P234A + A269G + S347N + Q385T | a630g; a1147t; g1148c; c1149a | + |
| 64 | L201F + G202F | | ++ |
| 65 | L201F + T241K | | ++ |
| 66 | L201F + G202Y | | ++ |
| 67 | L201F + S395T | | ++ |
| 68 | A30T + L201F | a300g | ++ |
| 69 | A118R + L201F | | ++ |
| 70 | S122V + L201F | | ++ |
| 71 | S122H + L201F | | ++ |
| 72 | L201F + P234A + S299P + Q378R | | +++ |
| 73 | S175Q + L201F | | +++ |
| 74 | S175L + L201F | | +++ |
| 75 | L201F + Q206L | | ++ |
| 76 | L201F + V219E | | ++ |
| 77 | L201F + V219R | | ++ |
| 78 | L201F + Q253M | | ++ |
| 79 | L201F + Q253A | | ++ |
| 80 | L201F + Q253S | | ++ |
| 81 | I180K + L201F | | ++ |
| 82 | I180C + L201F | | ++ |
| 83 | L201F + G216K | | ++ |
| 84 | L201F + D221L | | ++ |
| 85 | L201F + S233C | | ++ |
| 86 | L201F + V324H | | ++ |
| 87 | L201F + N282H + V324F | | ++ |
| 88 | L201F + N274K | | ++ |
| 89 | L201F + A276S + A366K | | ++ |
| 90 | A118R + L201F + P234A + S299P + Q378R + S395T | | ++++ |
| 91 | S122H + L201F + P203E + P234A + T241K + S299P + Q378R + S395T | | ++ |
| 92 | A118R + S122V + S175Q + L201F + P234A + T241K + S299P + Q378R + S395T | | ++++ |
| 93 | A118R + L201F + P203E + D220Y + P234A + T241K + S299P + Q378R + S395T | t1263c | +++ |
| 94 | L201F + D220Y + P234A + S299P + Q378R + S395T | | ++++ |
| 95 | S122V + L201F + P234A + T241K + S299P + Q378R + S395T | | ++++ |
| 96 | L201F + G202Y + P203E + D220Y + P234A + S299P + Q378R + S395T | | +++ |
| 97 | A118R + S175Q + L201F + D220Y + P234A + T241K + S299P + Q378R + S395T | | +++ |
| 98 | A118R + L201F + G202F + P234A + S299P + Q378R + S395T | | ++++ |

[1]Amino acid position determined by optimal alignment with SEQ ID NO: 4
[2]Nucleotide position determined by optimal alignment with SEQ ID NO: 3
[3]Fold improvement over native Ssp CBH2 (SEQ ID NO: 4) is represented as follows:
+ = 1.2 to 1.9 fold improvement over CBH2 of SEQ ID NO: 4;
++ = 2.0 to 2.9 fold improvement over CBH2 of SEQ ID NO: 4;
+++ = 3.0 to 3.9 fold improvement over CBH2 of SEQ ID NO: 4; and
++++ = >4.0 fold improvement over CBH2 of SEQ ID NO: 4.

Example 10

Characterization of Enzyme Stability

CBH2 polypeptide variants and native Ssp CBH2 were characterized to determine their stabilities at high temperature (60 and 65° C.) and low pH (pH 4.0 and 5.0) using the method of Example 6. The samples containing various CBH2 variant enzymes were pre-incubated at pH 5.0, 65° C. and pH 4.0, 60° C. for 0-24 hrs. The residual enzyme activity after the thermal challenge was measured using Avicel as substrate at pH 5, 65° C. for 48 hrs. Table 3 illustrates the residual activity of improved CBH2 variants at pH 5, 65° C. after pre-incubations for different lengths of time. The mutations listed in the table are indicated relative to SEQ ID NO: 4, the wildtype CBH2.

TABLE 3

Improved Ssp CBH2 variants.

| Amino Acid Mutations[1] | % residual activity after 8 mins @ pH 4.0, 60° C. | % residual activity after 1 hour @ pH 4.0, 60° C. | % residual activity after 6 hours @ pH 4.0, 60° C. |
| --- | --- | --- | --- |
| CBH2 native | 39 | 4 | 1 |
| Variant 72 (SEQ ID NO: 6) L201F + P234A + S299P + Q378R | 98 | 80 | 23 |

| Amino Acid Mutations[1] | % residual activity after 8 mins @ pH 5.0, 65° C. | % residual activity after 1 hour @ pH 5.0, 65° C. | % residual activity after 6 hours @ pH 5.0, 65° C. |
| --- | --- | --- | --- |
| CBH2 native | 10 | 2 | 0 |
| Variant 72 (SEQ ID NO: 6) L201F + P234A + S299P + Q378R | 86 | 22 | 4 |

[1]Amino acid position is determined by optimal alignment with SEQ ID NO: 4

Example 11

CBH2 Activity on Biomass Substrates

The activity of Ssp CBH2 and variants was determined on pretreated bagasse and pretreated corn stover. Percentage glucan available for hydrolysis for the biomass samples ranged from 32-60%. CBH2 enzyme was tested up to 1-29 g/l enzyme loading at substrate loads of 50-200 g/l. The reaction was incubated at pH 5.0-5.5 and temperatures of 55-75° C. for 48-72 hours. Reactions were quenched with 50% acetonitrile. Each plate was centrifuged, and the supernatant (150 μl) was collected and filtered through a 0.45 μm filter. Conversion of biomass substrates to soluble sugar oligomers was measured using an Agilent HPLC 1200 equipped with HPX-87H Ion exclusion column (300 mm×7.8 mm) with 5 mM $H_2SO_4$ at a flow rate of 0.6 ml/min at 65° C. The retention times of the cellobiose and glucose were 7.5 and 9.1 minute respectively. The percentage conversion with variant Sample No. 72 (SEQ ID NO: 6) is presented below in Table 4.

TABLE 4

| Variant CBH2 | % Conversion to soluble sugars (cellobiose + glucose) | |
| --- | --- | --- |
| (SEQ ID NO: 6) Enzyme load, % | Bagasse[1], 50 g/L | Corn stover[2], 56 g/l |
| 3.60 | 16.45 | 45.5 |
| 7.20 | 21.52 | 45.7 |

[1]60% glucan present;
[2]33% glucan present

It is understood that the examples and embodiments described herein are for illustrative purposes only and that various modifications or changes in light thereof will be suggested to persons skilled in the art and are to be included within the spirit and purview of this application and scope of the appended claims.

---

We claim:

1. An isolated *Streptomyces* sp cellobiohydrolase II (CBH2) polypeptide variant comprising:
    an amino acid sequence that is at least 90% identical to the wild type *Streptomyces* sp CBH2 of SEQ ID NO:-4 and comprises the substitution L201F, wherein the amino acid position is determined by optimal alignment with SEQ ID NO:-4, and wherein said CBH2 variant exhibits at least 2-fold improvement in cellulase activity compared to the wild-type *Streptomyces* sp. CBH2 set forth in SEQ ID NO:4.

2. The isolated CBH2 polypeptide variant according to claim 1, wherein the variant amino acid sequence is at least 95% identical to SEQ ID NO: 4.

3. The isolated CBH2 polypeptide variant according to claim 1, wherein the variant amino acid sequence is at least 97% identical to SEQ ID NO: 4.

4. The isolated CBH2 polypeptide variant according to claim 1, wherein the variant amino acid sequence is at least 99% identical to SEQ ID NO: 4.

5. The isolated CBH2 polypeptide variant of claim 1 further comprising a substitution at a position selected from A30, A118, S122, S175, I180, V183, G202, Q206, G216, V219, D221, S233, P234, T241, Q253, N274, V324, and/or S395.

6. The isolated CBH2 polypeptide variant according to claim 5, wherein the further substitution in the variant CBH2 polypeptide is selected from A30T, A118R, S122V/H, S175Q/L, I180K/C, V183G, G202F/Y, Q206L, G216K, V219E/R, D221L, S233C, P234S/A, T241R/K, Q253M/A/S, N274K/P, V324H/F and/or S395T.

7. The isolated CBH2 polypeptide variant of claim 1 further comprising a substitution at positions P234, S299 and Q378.

8. The isolated CBH7 polypeptide variant according to claim 7 wherein the substitution is selected from P234A, S299P, and Q378R.

9. The isolated CBH2 polypeptide variant of claim 1, wherein the variant amino acid sequence comprises at least 95% sequence identity to SEQ ID NO: 6 and optionally at least 1 further amino acid substitution[s].

10. The isolated CBH2 polypeptide variant of claim 1, wherein the variant exhibits at least 3-fold improvement in cellulase activity compared to wild type *Streptomyces* sp CBH2 set forth in SEQ ID NO: 4.

11. An isolated polynucleotide encoding the CBH2 polypeptide variant of claim 1.

12. The polynucleotide of claim 11 which has been codon optimized.

13. A vector comprising a polynucleotide according to claim 11.

14. A host cell transformed with vector of claim 13.

15. The host cell of claim 14, wherein the host cell is selected from a bacterial cell, a filamentous fungal cell or a yeast cell.

16. The host cell of claim 15, wherein the host cell is a bacterial cell.

17. The host cell of claim 16, wherein the host cell is a *Streptomyces* cell.

18. The host cell of claim 16, wherein the host cell is a *Bacillus* cell.

19. The host cell of claim 15, wherein the host cell is a filamentous fungal cell.

20. The host cell of claim 19, wherein the host cell is an *Aspergillus*, a *Chrysosporium*, a *Humicola*, a *Myceliopthora*, a *Neurospora*, a *Piromyces*, a *Thielavia*, or a *Trichoderma* host cell.

21. An enzyme composition comprising the CBH2 polypeptide variant of claim 1.

22. The enzyme composition of claim 21 further comprising additional cellulase enzymes.

23. The enzyme composition of claim 21 further comprising one or more additional enzymes selected from amylases, glucoamylases, esterases, cutinases, phytases, xylanases, lipases, and proteases.

* * * * *

UNITED STATES PATENT AND TRADEMARK OFFICE
CERTIFICATE OF CORRECTION

| | |
|---|---|
| PATENT NO. | : 8,785,170 B2 |
| APPLICATION NO. | : 13/393495 |
| DATED | : July 22, 2014 |
| INVENTOR(S) | : Dhawan et al. |

Page 1 of 1

It is certified that error appears in the above-identified patent and that said Letters Patent is hereby corrected as shown below:

In the Claims:

In claim 1, Column 57, Line 23, please replace "SEQ ID NO:-4" with --SEQ ID NO:4--.

In claim 1, Column 57, Line 26, please replace "SEQ ID NO:-4" with --SEQ ID NO:4--.

Signed and Sealed this
Seventh Day of October, 2014

Michelle K. Lee
*Deputy Director of the United States Patent and Trademark Office*